(12) United States Patent
Wang et al.

(10) Patent No.: US 11,097,000 B2
(45) Date of Patent: Aug. 24, 2021

(54) KLEBSIELLA PNEUMONIAE CAPSULE POLYSACCHARIDE VACCINES

(71) Applicants: NATIONAL TAIWAN UNIVERSITY, Taipei (TW); Academia Sinica, Taipei (TW)

(72) Inventors: Jin-Town Wang, Taipei (TW); Shih-Hsiung Wu, Taipei (TW); Chung-Yi Wu, Taipei (TW)

(73) Assignees: NATIONAL TAIWAN UNIVERSITY, Taipei (TW); ACADEMIA SINICA, Taipei (TW)

( * ) Notice: Subject to any disclaimer, the term of this patent is extended or adjusted under 35 U.S.C. 154(b) by 0 days.

(21) Appl. No.: 16/338,501

(22) PCT Filed: Oct. 3, 2017

(86) PCT No.: PCT/US2017/054978
§ 371 (c)(1),
(2) Date: Apr. 1, 2019

(87) PCT Pub. No.: WO2018/067596
PCT Pub. Date: Apr. 12, 2018

(65) Prior Publication Data
US 2020/0038497 A1    Feb. 6, 2020

Related U.S. Application Data

(60) Provisional application No. 62/403,365, filed on Oct. 3, 2016, provisional application No. 62/413,269, filed on Oct. 26, 2016.

(51) Int. Cl.
| | | |
|---|---|---|
| *A61K 39/108* | (2006.01) | |
| *A61K 31/04* | (2006.01) | |
| *C08B 37/00* | (2006.01) | |
| *A61P 31/04* | (2006.01) | |
| *A61K 39/00* | (2006.01) | |

(52) U.S. Cl.
CPC .......... *A61K 39/0266* (2013.01); *A61P 31/04* (2018.01); *C08B 37/006* (2013.01); *A61K 2039/6037* (2013.01); *A61K 2039/70* (2013.01)

(58) Field of Classification Search
CPC . A61K 39/0266; A61K 2039/70; A61P 31/04; C08B 37/006

USPC ....................................... 424/259.1
See application file for complete search history.

(56) References Cited

U.S. PATENT DOCUMENTS

| | | | | |
|---|---|---|---|---|
| 2008/0260773 | A1* | 10/2008 | Del Giudice | ........ A61K 39/107 |
| | | | | 424/196.11 |
| 2014/0295528 | A1* | 10/2014 | Wang | ..................... C07H 21/04 |
| | | | | 435/235.1 |

OTHER PUBLICATIONS

Pan et al. Genetic analysis of capsular polysaccharide synthesis gene clusters in 79 capsular types of *Klebsiella* spp. Scientific Reports 5:15573, Oct. 23, 2015. DOI: 10.1038/srep15573 (Year: 2015).*
Robert et al. Immunogenic Properties of Klebsiella pneumoniae Type 2 Capsular Polysaccharide. Infection and Immunity, Nov. 1986, vol. 54, No. 2, p. 365-370. (Year: 1986).*
Ho J-Y, Lin T-L, Li C-Y, Lee A, Cheng A-N, et al. (2011) Functions of Some Capsular Polysaccharide Biosynthetic Genes in Klebsiella pneumoniae NTUH K2044. PLoS ONE 6(7): e21664. doi:10.1371/journal.pone.0021664.
F.L. Yang et al., Structure and Immunological Characterization of the Capsular Polysaccharide of a Pyrogenic Liver Abscess Caused by Klebsiella pneumoniae, Activation of Macrophages Through Toll-Like Receptor, 4the Journal of Biological Chemistry vol. 286, No. 24, pp. 21041-21051, Jun. 17, 2011.
T.A. Ahmad et al.,Development of immunization trials against Klebsiella pneumoniae, Vaccine 30 (2012) 2411-2420.
Michael E Pichichero, Protein carriers of conjugate vaccines Characteristics, development, and clinical trials, Human Vaccines & Immunotherapeutics 9:12, 2505-2523; Dec. 2013; © 2013 Landes Bioscience Review.

* cited by examiner

*Primary Examiner* — Yih-Horng Shiao
(74) *Attorney, Agent, or Firm* — Hannah Tien

(57) ABSTRACT

The disclosure provides various immunogens comprising a repeat unit of saccharide of *Klebsiella pneumoniae* CPS, which has a formula selected from the group consisting of Formulae (I) to (VI) as described herein. Also provided are vaccines including one or more immunogens selected from Formula (I) to (VI) and methods of eliciting an immune response against a *Klebsiella pneumoniae* and preventing infection of *Klebsiella pneumoniae* by using an immunogen of the invention.

26 Claims, 15 Drawing Sheets
(3 of 15 Drawing Sheet(s) Filed in Color)
Specification includes a Sequence Listing.

K2 CPS +
K2-ORF16 protein (ng)

0   1   10   50   100   500   5000

KLEBSIELLA PNEUMONIAE CAPSULE POLYSACCHARIDE VACCINES

CROSS-REFERENCES TO RELATED APPLICATIONS

This patent application is a U.S. National Stage Application of PCT/US2017/054978 filed Oct. 3, 2017 and claims the benefit of priority from U.S. Provisional Application Ser. No. 62/403,365 filed Oct. 3, 2016, and from U.S. Provisional Application Ser. No. 62/413,269 filed Oct. 26, 2016, the contents of each of which is incorporated herein by reference in their entirety. Further, This application contains a Sequence Listing in computer readable form. The computer readable form is incorporated herein by reference.

FIELD OF THE INVENTION

The invention relates to the vaccine field. Particularly, the invention relates to a vaccine against *Klebsiella pneumoniae* infection comprising a conjugate of oligosaccharide units of capsular polysaccharides of *Klebsiella pneumoniae*.

BACKGROUND OF THE INVENTION

*Klebsiella pneumoniae* is an important pathogen which causes various diseases in human. Recently, community-acquired pyogenic liver abscess (PLA) caused by *K. pneumoniae* has become an emerging disease globally. The mortality rates are 10% among those with *K. pneumoniae*-caused PLA and 30-40% among those with metastatic meningitis. The survivors of metastatic meningitis usually have severe neurological sequelae and metastatic endophthalmitis usually resulting in blindness of the affected eyes. Besides causing PLA, *K. pneumoniae* also has been reported to cause invasive infections leading to abscesses at other sites (such as kidney, spleen, brain, and prostate), necrotizing fasciitis, and severe pneumonia with bacteremia.

Researchers report that the most common capsular type of the strains causing PLA is K1, and that the second is K2. In addition to these studies of PLA, recent studies demonstrate that the predominant capsular types of *K. pneumoniae* causing other invasive infections such as necrotizing fasciitis and bacteremic community-acquired pneumonia also are capsular type K1 and K2 (Lin Y T et al., *BMC infectious diseases* 2010, 10:307; and Fang C T et al., *Clinical infectious diseases: an official publication of the Infectious Diseases Society of America* 2007, 45(3):284-293).

Besides, *K. pneumoniae* is also responsible for approximate 10% of nosocomial infections and increasing resistances to antibiotics such as extended-spectrum β-lactams and carbapenem is also a significant problem. Our recent study reported that the capsular types K64 (38%), K62 (13%), K24 (8%), KN2 (7%) and K28 (6%) account for 72% of carbapenem resistant *K. pneumoniae* (CRKP). Clustering of capsular types in CRKP strains was observed.

Bacterial capsule-targeted vaccines, such as those for *Streptococcus pneumoniae*, are usually effective against infections caused by this encapsulated pathogen. A *K. pneumoniae* K1 capsule polysaccharide (CPS) vaccine has been reported in 1985. A 24-valent *K. pneumoniae* CPS vaccine has been also reported in 1988. Although *K. pneumoniae* K1 CPS and 24-valent CPS vaccine were reported several years ago, there was no available *K. pneumoniae* vaccine until now. Previous studies have demonstrated that the polysaccharide vaccine could only induce T-cell independent immunity which was lacking immunological memory as well as production of high affinity antibodies. Therefore, a *K. pneumoniae* CPS-protein conjugate vaccine would be more effective against infections caused by this bacterium.

K1 and K2 CPS composed with several repeat units of sugars were huge molecules (Yang F L et al., *The Journal of biological chemistry* 2011, 286(24):21041-21051). Depolymerization of CPS will increase the efficiency to conjugate with protein. Chemical reagents, such as trifluoroacetic acid, ammonium hydroxide and acetic acid, can reduce CPS units but result in loss of CPS modification (acetylation or pyruvation) which is important for immune responses. WO2012145676 A1 provides isolated bacteriophages which could infect K1 strains and have identified its capsule depolymerase specific to digest K1 CPS. There is a need to develop a vaccine against *Klebsiella pneumoniae* infection.

SUMMARY OF THE INVENTION

The invention utilizes digested capsular polysaccharides (CPSs) of *Klebsiella pneumoniae* separately conjugated with a carrier to generate CPS conjugate vaccines. The invention surprisingly found that the CPS conjugate vaccines could both induce CPS antibodies with bactericidal activities. The CPS conjugate vaccine can be applied in prevention of *K. pneumoniae* causing invasive infections.

The invention provides various immunogens comprising a repeat unit of saccharide of *Klebsiella pneumoniae* CPS, which has a formula selected from the group consisting of Formulae (I) to (VI) as described herein.

The invention provides an isolated polypeptide having degradation activity specific to the capsule of *Klebsiella pneumoniae* capsular type K2 strains, selected from the group consisting of: (a) a polypeptide comprising the amino acid sequence of SEQ ID NO: 2; and (b) a polypeptide which is encoded by a polynucleotide which hybridizes under at least high stringency conditions with (i) the polypeptide coding sequence of SEQ ID NO: 2, or (ii) a full-length complementary strand of (i).

The invention also provides a vaccine comprising one or more immunogens selected from Formula (I) to (VI).

Certain embodiments include vaccines comprising an immunogen conjugated with a protein carrier. In further embodiments, the vaccine is a K1 and K2 CPS conjugated divalent vaccine comprising immunogens of Formula I and Formula II, or a K64 and K62 CPS conjugated divalent vaccine comprising immunogens of Formula III and Formula IV.

The present invention provides a method of eliciting an immune response against a *Klebsiella pneumoniae*, comprising administering an effective amount of the immunogen of the invention or a vaccine of the invention.

The present invention also provides an antibody produced by administering the conjugate vaccine of the invention.

The present invention also provides a method of preventing infection of *Klebsiella pneumoniae*, comprising administering an effective amount of the immunogen of the invention or a vaccine of the invention.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
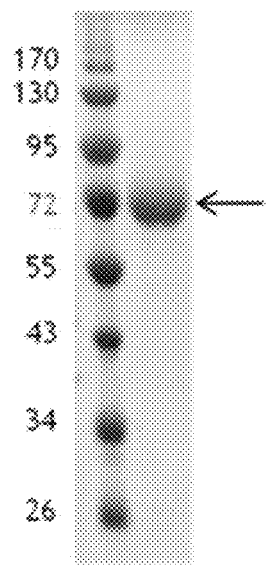
FIGS. 1 (A) to (C) show the enzymatic activity of purified K2-ORF16 protein. (A) The purified K2-ORF16 protein (indicated with the arrow) was separated on SDS-PAGE gel with Coomassie blue staining and the sizes (kilo-daltons) were indicated beside the protein marker. (B) A clear spot surrounding with a translucent halo and a translucent spot are observed when the phage 1611E-K2-1 (left) and its K2-ORF16 (right) protein were spotted on the plate overlaid with top agar containing *K. pneumoniae* 1611E strain, respectively. (C) The extracted K2 CPS treated with various amounts of K2-ORF16 protein were separated on SDS-PAGE gel with alcian blue staining.

Unless otherwise noted, technical terms are used according to conventional usage.

The singular terms "a," "an," and "the" include plural referents unless context clearly indicates otherwise. Similarly, the word "or" is intended to include "and" unless the context clearly indicates otherwise.

Abbreviations: GlcAp: glucuronic acid; Fucp: fucose; Glcp: glucose; Manp: mannose; Rhap: rhamnose; Galp: galactose; GlcUAp: GlcAp: glucuronic acid.

As used herein, the term "conjugate" refers to a composition composed of two heterologous molecules linked together useful for stimulating or eliciting a specific immune response in an animal. In some embodiments, the immune response is protective in that it enables the animal to better resist infection from the organism against which the immunogenic conjugate is directed. One specific example of a type of immunogenic conjugate is a vaccine, such as a conjugate vaccine.

As used herein, the term "linker" refers to a compound or moiety that acts as a molecular bridge to operably link two different molecules, wherein one portion of the linker is operably linked to a first molecule and wherein another portion of the linker is operably linked to a second molecule. The two different molecules can be linked to the linker in a step-wise manner.

As used herein, the term "vaccine" refers to a pharmaceutical composition that elicits a prophylactic or therapeutic immune response in a subject. Typically, a vaccine elicits an antigen-specific immune response to an antigen of a pathogen.

As used herein, the term "oligosaccharide" refers to a compound containing two or more monosaccharide units. Oligosaccharides are considered to have a reducing end and a non-reducing end.

As used herein, "protein carrier" refers to a protein, peptide or fragment thereof, which is coupled or conjugated to an oligosaccharide to enhance the immunogenicity of the resulting oligosaccharide-protein carrier conjugate to a greater degree than the oligosaccharide alone.

As used herein, the term "antibody" encompasses polyclonal and monoclonal antibody preparations, as well as preparations including hybrid antibodies, altered antibodies, F(ab').sup.2 fragments, F(ab) molecules, Fv fragments, single chain fragment variable displayed on phage (scFv), single domain antibodies, chimeric antibodies, humanized antibodies, and functional fragments thereof which exhibit immunological binding properties of the parent antibody molecule.

As used herein, the term "immunogen" refers to a protein or a portion thereof that is capable of inducing an immune response in a mammal, such as a mammal infected or at risk of infection with a pathogen. Administration of an immunogen can lead to protective immunity and/or proactive immunity against a pathogen of interest.

In one aspect, the invention provides an immunogen comprising a repeat unit of trisaccharide of *Klebsiella pneumoniae* K1 CPS, which has the following Formula (I):

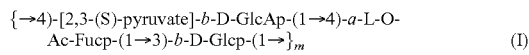

wherein m is 1 to 4.

In one embodiment, m is 2.

The invention found that K1-orf34 polypeptide can degrade *Klebsiella pneumoniae* K1 CPS. After the degradation, a hexasaccharide of *Klebsiella pneumoniae* K1 CPS can be obtained. The hexasaccharide degraded from K1 CPS can be used an immunogen against *Klebsiella pneumoniae* infection. The K1-orf34 polypeptide has an amino acid sequence as shown in SEQ ID NO:1.

(SEQ ID NO: 1)
MALIRLVAPERVFSDLASMVAYPNFQVQDKITLLGSAGGDFTFTTTASVV

DNGTVFAVPGGYLLRKFVGPAYSSWFSNWTGIVTFMSAPNRHLVVDTVLQ

ATSVLNIKSNSTLEFTDTGRILPDAAVARQVLNITGSAPSVFVPLAADAA

AGSKVITVAAGALSAVKGTYLYLRSNKLCDGGPNTYGVKISQIRKVVGVS

TSGGVTSIRLDKALHYNYYLSDAAEVGIPTMVENVTLVSPYINEFGYDDL

NRFFTSGISANFAADLHIQDGVIIGNKRPGASDIEGRSAIKFNNCVDSTV

KGTCFYNIGWYGVEVLGCSEDTEVHDIHAMDVRHAISLNWQSTADGDKWG

EPIEFLGVNCEAYSTTQAGFDTHDIGKRVKFVRCVSYDSADDGFQARTNG

VEYLNCRAYRAAMDGFASNTGVAFPIYRECLAYDNVRSGFNCSYGGGYVY

DCEAHGSQNGVRINGGRVKGGRYTRNSSSHIFVTKDVAETAQTSLEIDGV

SMRYDGTGRAVYFHGTVGIDPTLVSMSNNDMTGHGLFWALLSGYTVQPTP

PRMSRNLLDDTGIRGVATLVAGEATVNARVRGNFGSVANSFKWVSEVKLT

RLTFPSSAGALTVTSVAQNQDVPTPNPDLNSFVIRSSNAADVSQVAWEVY

L

In another aspect, the invention provides an immunogen comprising a repeat unit of tetrasaccharide of *Klebsiella pneumoniae* K2 CPS, which has the following Formula (II):

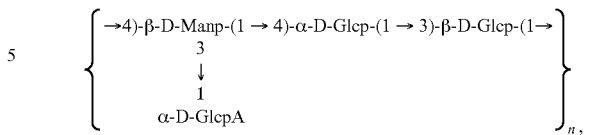

wherein n is 1 to 4.

In one embodiment, the immunogen contains one repeat unit (i.e., n is 1).

The invention found that K2-ORF16 polypeptide can degrade *Klebsiella pneumoniae* K2 CPS. After the degradation, a tetrasaccharide of *Klebsiella pneumoniae* K2 CPS can be obtained. The tetrasaccharide degraded from K2 CPS can; used an immunogen against *Klebsiella pneumoniae* infection. Accordingly, the invention provides an isolated polypeptide or a variant thereof, having degradation activity specific to the capsule of *Klebsiella pneumoniae* capsular type K2 strains, selected from the group consisting of: (a) a polypeptide comprising the amino acid sequence of SEQ ID NO: 2; and (b) a polypeptide which is encoded by a polynucleotide which hybridizes under at least high stringency conditions with (i) the polypeptide coding sequence of SEQ ID NO: 2, or (ii) a full-length complementary strand of (i). In one embodiment, the K2-ORF16 polypeptide has an amino acid sequence as shown in SEQ ID NO:2.

(SEQ ID NO: 2)
MTIIKRADLGRPLTWDELDDNFQQVDDLTAAASAAVLSASASATAAAGSA

TNSLNSANSAASSADDAAASATVAINALMNSTFEPADFDFTSGGTLDSTD

RNKAVYNPADNNWYSWSGILPKIVTAATDPTADSNWKPRTDQLLRQNLAS

SVIPGTSLVTHSDGIHLDDYIEIFNRRTKFIMPEDFPGTDTEQLQSALSY

AKSNRVNVVLQAGKTYYVTGSQGLEVDLGYYSFESPNGIAYIDFTGCTAT

YCLWVHSSRPYPDGSENHCTSMRGIKFKSSVKGIGQRLLLTGNNNDSSNG

TYNGDCKIENCMFSTADIVLGASNSTWRYKFINCGFMMESTGGTYAMHFP

AGISDSGESVTFQNCKIFDMKGCPILVECASFAIGMPGTSVLNTPIKITG

SGAMVIMDSAANIENPGASAWYRYGEVTGTGARLILNGCTLVCNNPSLQT

KPLFYVGANAFIDVTLVKTPGNDYLFQNGDEGLRTFVEGDGYVTASHCIG

DILSGVGNIPLHKSLNPTLNPGFETGDLSSWSFNNQGSASQTCVVGTAYK

KTGTYGARMTSFGSLSCFLTQKVKVTQHGYYSTTCQINTITAGTGTTAGS

LTITFYNRDGNALQAGASSNFTNTPSGWQSVGRFIQGRVPQAAEYCEVSF

RCREGAVIDVDNFIINFT

The variant of the polypeptide is artificial, which comprises a substitution, deletion, and/or insertion of one or more amino acids of the polypeptide of SEQ ID NO:2. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a tract of histidine tag or a tract of poly-histidine tag, an antigenic epitope or a binding domain In another aspect, the invention provides an immunogen comprising a repeat unit of hexasaccharide of *Klebsiella pneumoniae* K64 CPS, which has the following Formula (III):

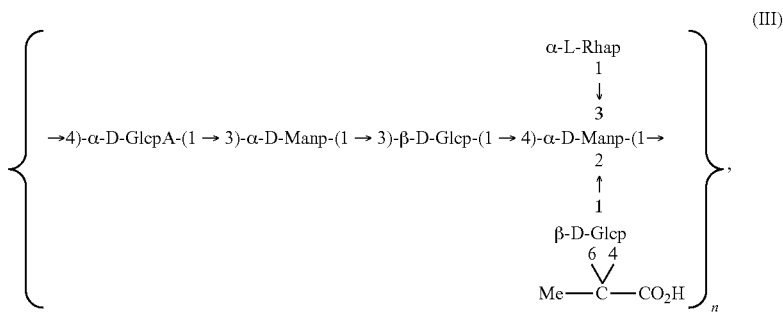

(III)

wherein n is 1 to 4. In one embodiment, n is 1.

In another aspect, the invention provides an immunogen comprising a repeat unit of pentasaccharide of *Klebsiella pneumoniae* K62 CPS, which has the following Formula (IV):

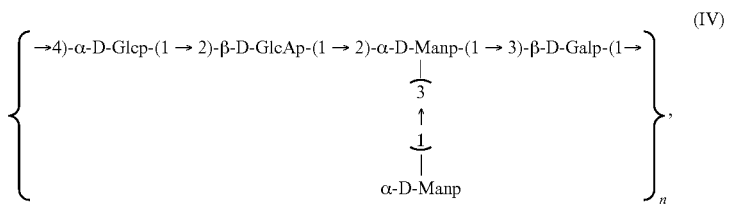

(IV)

wherein n is 1 to 4. In one embodiment, n is 2.

In another aspect, the invention provides an immunogen comprising a repeat unit of pentasaccharide of *Klebsiella pneumoniae* K24 CPS, which has the following Formula (V):

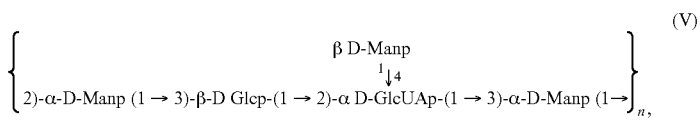

(V)

wherein n is 1 to 4. In one embodiment, n is 1.

In another aspect, the invention provides an immunogen comprising a repeat unit of hexasaccharide of *Klebsiella pneumoniae* K28 CPS, which has the following Formula (VI):

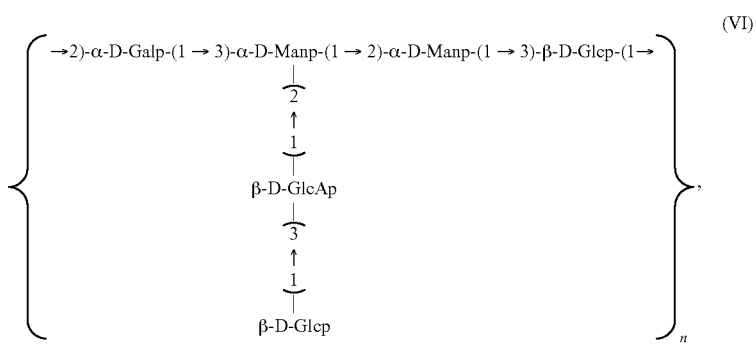

(VI)

wherein n is 1 to 4. In one embodiment, n is 1.

In another aspect, the invention provides an immunogen comprising a repeat unit of hexasaccharide of *Klebsiella pneumoniae* KN2 CPS, which has four hexoses and one hexuronic acid and about a molecule weight of about 1027.

The enzymes used for degrading CPS of K24, K28, K62, K64 and KN2 are described in WO2012145676 A1.

In another aspect, the invention provides a vaccine comprising one or more immunogens selected from Formula (I) to (VI).

The structural sugar units and the degraded CPS products of K1, K2, K62, K64, K24 and K28 are as follows.

|  | Structural sugar units | Degraded CPS products |
| --- | --- | --- |
| K1 | Tri-saccharides | Hexasaccharide (two units) |
| K2 | Tetra-saccharides | Tetrasaccharide (one unit) |
| K62 | Penta-saccharide | Decasaccharide (two units) |
| K64 | Hexa-saccharide | Hexasaccharide (one unit) |
| K24 | Penta-saccharide | Pentasaccharide (one unit) |
| K28 | Hexa-saccharide | Hexasaccharide (one unit) |

In one embodiment, the immunogen is conjugated with a protein carrier.

In one embodiment, the vaccine is a multi-valent vaccine. In some embodiments, the vaccine is a K1 and K2 CPS conjugated divalent vaccine comprising immunogens of Formula I and Formula II. In a further embodiment, the vaccine is a K1 and K2 CPS conjugated divalent vaccine comprising a mixture of immunogen I-carrier and immunogen II-carrier, wherein the immunogen I having Formula (I) and the immunogen II having Formula (II) are conjugated with a carrier, respectively.

In one embodiment, the vaccine is a multi-valent vaccine. In some embodiments, the vaccine is a K64 and K62 CPS conjugated divalent vaccine comprising immunogens of Formula III and Formula IV. In a further embodiment, the vaccine is a K64 and K62 CPS conjugated divalent vaccine comprising a mixture of immunogen III-carrier and immunogen IV-carrier, wherein the immunogen III having Formula (III) and the immunogen IV having Formula (IV) are conjugated with a carrier, respectively.

The immunogen of the invention can be conjugated with a carrier to form a conjugate. In one embodiment, the conjugate is a vaccine. In another embodiment, any one of the immunogen ratio in the conjugate vaccine is from 1:1.4 to 1:10.2. In one embodiment, the vaccine comprises 10% (w/w) to 90% (W/W) of immunogen I or III-protein carrier and 10% (w/w) to 90% (W/W) of immunogen II- or IV-carrier. Preferably, the vaccine comprises equal amount of immunogen I- or III-carrier and immunogen II- or IV-carrier.

Suitable carriers are known in the art and may include, for example, proteins, peptides, lipids, polymers, dendrimers, virosomes, virus-like particles (VLPs), or combinations thereof. In one embodiment, the carrier is a protein carrier, including but are not limited to, bacterial toxoids, toxins, exotoxins, and nontoxic derivatives thereof, such as keyhole limpet hemocyanine (KLH), hepatitis B virus core protein, thyroglobulin, albumins (such as bovine serum albumin (BSA), human serum albumin (HSA), and ovalbumin), pneumococcal surface protein A (PspA), pneumococcal adhesion protein (PsaA), purified protein derivative of tuberculin (PPD); transferrin binding proteins, polyamino acids, such as poly(lysine:glutamic acid), tetanus toxoid, tetanus toxin Fragment C, diphtheria toxoid, CRM (a nontoxic diphtheria toxin mutant), cholera toxoid, *Staphylococcus aureus* exotoxins or toxoids, *Escherichia coli* heat labile enterotoxin, *Pseudomonas aeruginosa* exotoxin A and bacterial outer membrane proteins (such as *Neisseria meningitidis* serotype B outer membrane protein complex (OMPC) and outer membrane class 3 porin (rPorB)).

In one embodiment, the carrier is a protein carrier. In a further embodiment, the protein carrier is CRM197. The amino acid sequence of CRM197 is shown in SEQ ID NO:3.

(SEQ ID NO: 3)
GADDVVDSSKSFVMENFSSYHGTKPGYVDSIQKGIQKPKSGTQGNYDDDW

KEFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSSSEKIH

SNEISSDSIGVLGYQKTVDHTKVNSKLSLFFEIKS

Polysaccharides contain hydroxyl groups, and occasionally carboxyl and amino groups, and proteins contain amino and carboxyl groups. Many methods are known in the art for conjugating a protein to a polysaccharide. If the protein carrier is the same for two or more saccharides in the composition, the saccharides could be conjugated to the same molecule of the protein carrier. Alternatively the saccharides may each be separately conjugated to different molecules of the protein carrier (each molecule of protein carrier only having one type of saccharide conjugated to it).

The amount of vaccine of the invention to be administered a human or animal and the regime of administration can be determined in accordance with standard techniques well known to those of ordinary skill in the pharmaceutical and veterinary arts taking into consideration such factors as the particular antigen, the adjuvant (if present), the age, sex, weight, species and condition of the particular animal or patient, and the route of administration.

The disclosed conjugate vaccine can be delivered to a subject in a manner consistent with conventional methodologies used in treatment or prevention, for example infection from *Klebsiella pneumoniae*. In accordance with the disclosure herein, a prophylactically or therapeutically effective amount of the conjugate vaccine and/or other biologically active agent is administered to a subject in need of such treatment for a time and under conditions sufficient to prevent, inhibit, and/or ameliorate a *Klebsiella pneumoniae* infection. In some embodiments, administration of the conjugate vaccines to a subject elicits an immune response against a *Klebsiella pneumoniae* antigenic immunogen in the subject. In some embodiments, a subject is selected for treatment that has, or is at risk for developing, a *Klebsiella pneumoniae* infection, for example because of exposure or the possibility of exposure to a *Klebsiella pneumoniae*. In an important aspect, the conjugate vaccine provided herein may be used to prevent infection of *Klebsiella pneumoniae*.

The conjugate vaccine may be prepared as a solution, suspension, tablet, pill, capsule, sustained release formulation, powder, or the like. The antigens and immunogenic composition may be mixed with physiologically acceptable carriers which are compatible therewith. These may include water, saline, dextrose, glycerol, ethanol, combinations thereof, and the like. The conjugate vaccine may further contain auxiliary substances, such as wetting or emulsifying agents or pH buffering agents, to further enhance the effectiveness. Administration of the conjugate vaccine can include delivery by various routes, such as, for example, oral, intravenous, intramuscular, nasal, subcutaneous, and intraperitoneal administration.

In a further aspect, the invention provides an antibody produced by administering the conjugate vaccine of the invention.

The examples that follow are intended to illustrate the invention and not to limit it. All percentages used herein are by weight unless otherwise indicated. All patents, patent applications, and literature references cited herein are hereby incorporated by reference in their entirety.

EXAMPLES

Materials and Methods
Phage Isolation
Agar overlay method was used for isolation of a pure phage preparation and titer determination of the phage. The infectivity of the phage was determined using a spot test (Lin T L, Hsieh P F, Huang Y T, et al. *Isolation of a bacteriophage and its depolymerase specific for K1 capsule of Klebsiella pneumoniae: implication in typing and treatment. The Journal of infectious diseases* 2014; 210:1734-44).

Phage Genomic DNA Preparation and Sequencing
Phage genomic DNA was extracted per Qiagen Lambda kit with modifications as follows (Lin T L, Hsieh P F, Huang Y T, et al. *Isolation of a bacteriophage and its depolymerase specific for K1 capsule of Klebsiella pneumoniae: implication in typing and treatment. The Journal of infectious diseases* 2014; 210:1734-44). After phages were precipitated and lysed, the DNA was extracted by phenol/chloroform and precipitated with ethanol. The genome sequences of the phage were determined by Illumina GAII sequencing.

Protein Expression and Purification
The recombinant His-tagged K1-ORF34 protein was expressed and purified according to a recent study (Lin T L, Hsieh P F, Huang Y T, et al. *Isolation of a bacteriophage and its depolymerase specific for K1 capsule of Klebsiella pneumoniae: implication in typing and treatment. The Journal of infectious diseases* 2014; 210:1734-44). The K2-orf16 was amplified by PCR using primers 1611E-ORF16-F (5'-CAAACATCACGGTGAC GCTAGCATGACCATTATCAAACG-3'; SEQ ID NO: 4) and 1611E-ORF16-R (5'-CTTTTAACATTTAGCA CTCGAGTGTAAAATTAATAATG-3'; SEQ ID NO: 5) and then digested with NheI and XhoI. The K2-orf16 fragment was cloned into the NheI and XhoI double-digestion site of a pET28c plasmid (Novagen). The K62 capsule depolymerase was amplified by PCR using primers Ref-K10-1 ORF6-F (5'-ATGAATAAGATGTTTACCCAG-3'; SEQ ID NO: 6) and Ref-K10-1 ORF6-R (5'-AAT-TGGGCGAAGGCGTTCAAAC-3'; SEQ ID NO: 7) and then cloned into the blunted EcoRI site of a pET28c plasmid (Novagen). The resulting plasmids were transformed into *E. coli* BL21 (DE3). The recombinant His-tagged proteins were expressed by inducing with 0.4 mM IPTG for overnight at 16° C., and were purified per the manufacturer's protocol (Qiagen).

Purification of *K. pneumoniae* CPS
The K1, K2 and K62 CPS were purified from *K. pneumoniae* NTUH-K2044 ΔwbbO, NTUH-A4528 ΔwbbO and K62 reference ΔwbbO mutant strains (Hsieh P F, Lin T L, Yang F L, et al. Lipopolysaccharide O1 antigen contributes to the virulence in *Klebsiella pneumoniae* causing pyogenic liver abscess. PloS one 2012; 7:e33155), respectively, in order to eliminate the contamination of O polysaccharide. The bacteria were cultured on Luria agar plate over 12 hours at 37° C. The bacteria lawn was scrapped, collected and put in sterilized water (w/v=1/10), and heated at 100° C. for 10 minutes. After cooling, the bacterial solution was centrifuged at 15,000×g for 20 minutes. The supernatant (volume) was mixed with ice-cold acetone (4×volumes) for polysaccharide precipitation. After centrifugation at 12,000×g for 20 minutes, the pellet was the crude CPS. The pellet was suspended in sterilized water and lyophilized. The crude CPS powder was digested by ribonuclease (Roche) and deoxyribonuclease I (Roche) for 24 hours at 37° C. and then with protease K in 10 mM Tris-HCl, pH 7.4 for further 6-8 hours. After denaturation at 100° C. for 10 minutes, the supernatant was then dialyzed extensively against water using an 8-10 kDa cutoff membrane and lyophilized. The partial purified CPS was further purified on a TSK HW-65F column [1.6 cm (diameter)×90 cm (height)] by eluting with 0.1% sodium azide in filtered $H_2O$. Fractions containing carbohydrates were detected by phenol-sulfuric acid method and dialyzed against $H_2O$ (MW cutoff: 1 kDa), and concentrated by lyophilization.

CPS Structure Analysis
The chemical structures of *K. pneumoniae* NTUH-K2044 (1(1) and A4528 (K2) capsular polysaccharide could be followed by the previous studies (Yang F L et al., *The Journal of biological chemistry* 2011, 286(24):21041-21051; Corsaro M M et al., *Carbohydrate research* 2005, 340(13):2212-2217).

Mass Spectrometry:
For MALDI MS analysis, 0.5 μL of sample was mixed with 0.5 μL of matrix solution (20 mg/mL 2,5-dihydroxybenzoic acid (DHB) in 50% ACN and 1% $H_3PO_4$), spotted onto stainless steel plates, air-dried, and then analyzed on a 4800 MALDI TOF/TOF Analyzer (Applied Biosystems, Foster City, Calif.). It was carried out in the positive reflector mode with an acceleration voltage of 20 kV, 16% grid voltage. A typical spectrum was generated by 1,000 laser shots. The raw spectra were processed by baseline subtraction and noise removal using Data-Explorer software (Applied Biosystems) (Tsai C F et al., *Neuromethods* 2011, 57:181-196). For mass spectrum analysis, measurements were performed on an Ultraflex II MALDI-TOF/TOF mass spectrometer (Bruker Daltonik GmbH, Germany). Mass spectra were obtained in the range of mass to charge ratio (m/z) from 500 to 4,000 with reflector mode. MS/MS analysis was performed in the LIFT mode. Mass spectrometry analyses were performed by GRC Mass Core Facility of Genomics Research Center, Academia Sinica, Taipei, Taiwan.

NMR Spectra:
The NMR spectra of small CPS fragments in $D_2O$ were recorded; all two-dimensional NMR experiments were carried out with standard pulse sequences provided by Bruker. NMR data were processed using topspin 3.1. NMR experiments and resonance assignments: All NMR experiments are carried out on a Bruker AVANCE 600 or AVANCE 800 NMR spectrometer (Bruker, Karlsruhe, Germany) equipped with a triple ($^1H$, $^{13}C$ and $^{15}N$) resonance cryoprobe, including a shielded z-gradient. Two dimensional (2D) $^1HNMR$, TOCSY and NOESY spectra are collected. All heteronuclear NMR experiments for recombinant protein were carried out as required. Sequence-specific assignment of the backbone atoms is achieved by independent connectivity analysis of CBCA(CO)NH, HNCACB, HNCO, HN(CA)CO, and C(CO)NH. The 1H resonances are assigned using 3D HAHB(CO)NH and HCCH-TOCSY.

Enzymatic Cleavage:

K1 CPS was degraded by K1 lyase through β-elimination to produce the double bond between C-4 and C-5 of glucuronic acid, which was detected the change of absorption at 232 nm spectrophotomerically. Assay was performed at 25° C. in triplicate in 1-ml-volumn cuvette in a UV-VIS spectrophotometer (Ultrospec 4000 UV/Visible; Amersham Pharmacia Biotech, Piscataway, N.J., USA). Recommbination K1 lyase (10 μg/ml) was added into the reaction mixture containing 25 mM Tris pH7.5, 3 mM MgCl2 and 40 μg/ml CPS. The increase of absorption at 232 nm was then followed for 15 minutes. Reference cuvettes contained no K1 lyase.

Quantification of Reducing Ends with 3,5-Dinitrosalicylic Acid (DNSA) Assay (for K2 Hydrolase):

Hydrolase activity was determined by estimating the concentration of reducing sugars by 3,5-dinitrosalicyclis acid (DNAS)(Sigma-Aldrich) method (Danner M et al., *European journal of biochemistry/FEBS* 1993, 215(3): 653-661; Miller G L et al., *Analytical Chemistry* 1959, 31(3): 426-428). When sample was mixed with DNSA and heated to catalyze the reaction, the nitro group in 3' position of DNS would be reduced to amine whose absorbance can be measured at 535 nm by apparatus FlexStation 3. Through quantification the concentration of reducing sugar, the optimal condition for each hydrolase could be determined.

Capillary Electrophoresis:

Capillary electrophoresis was performed on a Beckman P/ACE MDQ Capillary Electrophoresis system equipped with a UV detector set at 230 nm. Separation and analysis were performed by a electrokinetic chromatography coated a fused-silica capillary tube (77 μm ID, 65 cm total length, and 50 cm from the injection point to the detector) at 25° C. The operating buffer was consisted of sodium phosphate buffer (50 mM, pH 9.0). The buffer was degassed by vacuum filtration through a 0.2 μm membrane filter, and shaken in an ultrasonic bath. Before each run, the capillary tube was washed with 0.1 M NaOH for 5 minutes, double-distilled water for 5 minutes, and then conditioned with the operating buffer for 5 minutes. The samples to be analyzed were injected automatically, using the pressure injection mode, in which the sample was pressurized for 15 seconds. Capillary electrophoresis was performed at 20 kV (about 65 mA) using a normal polarity.

Conjugations of Digested CPS with DT-CRM197 Carrier Protein

General Procedure for the Preparation of Glycosyl Amines Via Kochetkov Amination:

To a solution of a reducing sugar (20 mg) in 3.0 mL of DD water was added ammonium carbonate (3.0 g, excess). The resulting suspension was sealed, and stirred at room temperature for 7 days. The reaction mixture was freeze dried until the dry weight of the residue remains constant. These glycosyl amines were obtained as colorless solids, and were used without further purification.

General Procedure for the Attachment of Thiol Linker Via Glycosyl Amine:

To a solution of the above glycosyl amines (20 mg) in 3.0 mL of PBS buffer (pH 7.4) was added DTSSP (20 mg, excess). The reaction mixture was maintained at pH 7.4-7.8 by adding 1M NaOH solution, and stirred at room temperature for 16 hrs. To the above solution was added DTT (20 mg, excess), and the mixture stirred at 40° C. for 1-2 hrs. The solvent was removed under reduced pressure, and the residue was purified by chromatography on a column of Sephadex LH-20 eluded with DD water to afford the desired products digested CPS-SH.

The Synthesis of CRM197-Maleimid:

After the salt of commercial CRM197 (1.0 mg) was removed via alternate dissolving in water and dialyzing (Amicon Ultra-0.5, 10 kDa), the residue was dissolved in PBS buffer (pH 6.5, 1.0 mL) and transferred into a sample vial. Sulfo-EMCS (1.0 mg, $8.22 \times 10^{-6}$ mol) was added to the solution, and then the reaction was kept stirring at room temperature for 2 hours. The mixture was purified by Amicon Ultra-0.5 (10 kDa). After using MALDI-TOF to check the molecular weight and BCA assay to calculate the amount of protein, the CRM197-maleimid was stored in PBS buffer (pH 7.2, 1.0 mg/mL) for next step. According to the data of MALDI-TOF, the amount of maleimid function groups could be calculated. For example, when the molecular weight of CRM197-maleimid was 61841, the numbers of maleimide function groups on CRM197-maleimid can be determined.

The Synthesis of Digested CPS-CRM197 Conjugates (1~4):

The CRM197-maleimids were dissolved in PBS buffer (pH 7.2, the concentration was 1.0 mg/mL) and then different amount of digested CPS-SH (5.0 mg/mL in PBS buffer, pH 7.2) were added into the solution. The mixtures were stirred at room temperature for 2 hours. The digested CPS-CRM197 conjugates were purified by using Amicon Ultra-0.5 (10 kDa) to remove the nonreactive digested CPS-SH and sodium phosphate salt via dialysis. The obtained digested CPS-CRM197 conjugates could be characterized by MALDI-TOF analysis to determine the carbohydrate incorporation rate. The nonreactive digested CPS-SH could be recovered after reacting with DTT and purifying by LH-20 column chromatography. By changing the amount of used digested CPS-SH, we can conjugate different epitope ratios of oligosaccharides to the CRM197 carrier.

Vaccination

The CPS conjugated vaccine was diluted to 100 μg/ml in PBS and the glycolipid adjuvant C34 was dissolved to 100 μg/ml in DMSO. Mice were intra-muscular (IM) inoculated with 100 μl vaccine mixture composed of CPS conjugated vaccine (2 μg glycan) and 2 μg adjuvant. For K1 and K2 vaccines: Five-week old female BALB/c mice were received vaccine three times with one-week interval. For K62 vaccine: Five-week old female BALB/c mice were received vaccine five times with two-week interval.

Detection of Antibody Against CPS

Different amounts of purified CPS were transferred onto membrane by dot blotting. Antibodies against CPS were detected by incubating sera from vaccinated mice (1:1000 dilution).

Serum Bactericidal Assay

The mice sera after treatment at 56° C. for 30 min were two-fold serial diluted (1/2 to 1/256) with normal saline. The 25 μl of diluted sera and 12.5 μl of bacteria suspension (100 CFU) were incubated at 37° C. for 15 minutes. After incubation, 12.5 μl of newborn rabbit complement (Pel-Freez, USA) were added and incubated for 1 hour at 37° C. Then the reaction mixture was plated on the LB plate. After overnight culture, the numbers of surviving bacteria were counted. Serum bactericidal titers were defined as the reciprocal of the serum dilution that resulted in 50% killing of the bacteria that achieved with the bacteria-complement-sera from mice with inoculation of adjuvant only controls.

Protection Assay

For K1 and K2 vaccines: Vaccinated or control mice (adjuvant only) were intraperitoneal (IP) inoculated with $1\times10^4$ CFU of NTUH-K2044 or NTUH-A4528 at one week after vaccination (5 mice each group). The mortality of mice was observed for 30 days. Survival was analyzed by Kaplan-Meier analysis with a log-rank test; a P value<0.05 was considered statistically significant. For K62 vaccine: Vaccinated or control mice (adjuvant only) were IP pre-treated with cyclophosphamide twice at a dose of 100 mg/kg, at 2-day intervals. The cell counts of white blood cell and neutrophil were significantly decreased in cyclophosphamide treated mice. These mice were IP inoculated with $5\times10^6$ CFU of K62 reference strain at two days after cyclophosphamide treatment (5 mice each group). The mortality of mice was observed for 30 days. Survival was analyzed by Kaplan-Meier analysis with a log-rank test; a P value<0.05 was considered statistically significant. Vaccines comprising other immunogen(s) as described herein are assayed according to similar method as mentioned above.

Example 1 Isolation of Phage Infecting the *K. pneumoniae* 1611E Strain (Capsular Type K2)

The previous study identified a K1 capsule depolymerase (K1-ORF34) from a K1 specific phage NTUH-K2044-K1-1 (Lin T L et al., *The Journal of infectious diseases* 2014, 210(11):1734-1744). In order to isolate K2 capsule degrading enzymes, phage infecting *K. pneumoniae* 1611E strain (capsular type K2) were isolated from untreated water. Clear plaques with translucent halos were detected and the phage was designated 1611E-K2-1. The sensitivity for capsular type K2 of 1611E-K2-1 phage was evaluated among another 7 capsular type K2 strains whose capsular type was determined by PCR using wzy primers. This phage could infect all strains with capsular type K2.

Example 2 Identification of the Putative Capsule Depolymerases

Identification of the Putative K2 Capsule Depolymerase

Figure 1B:
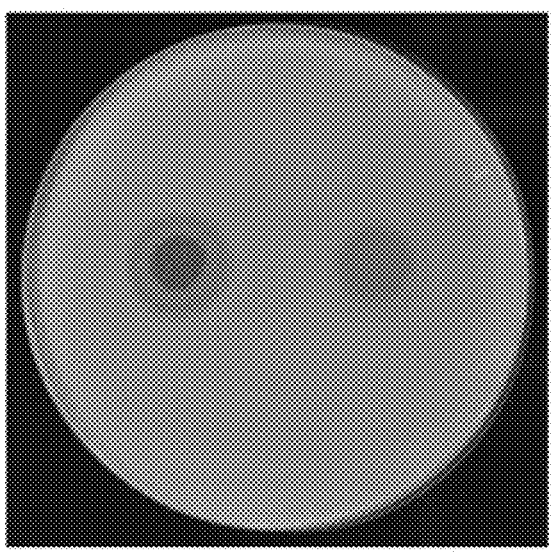
Figure 1C:
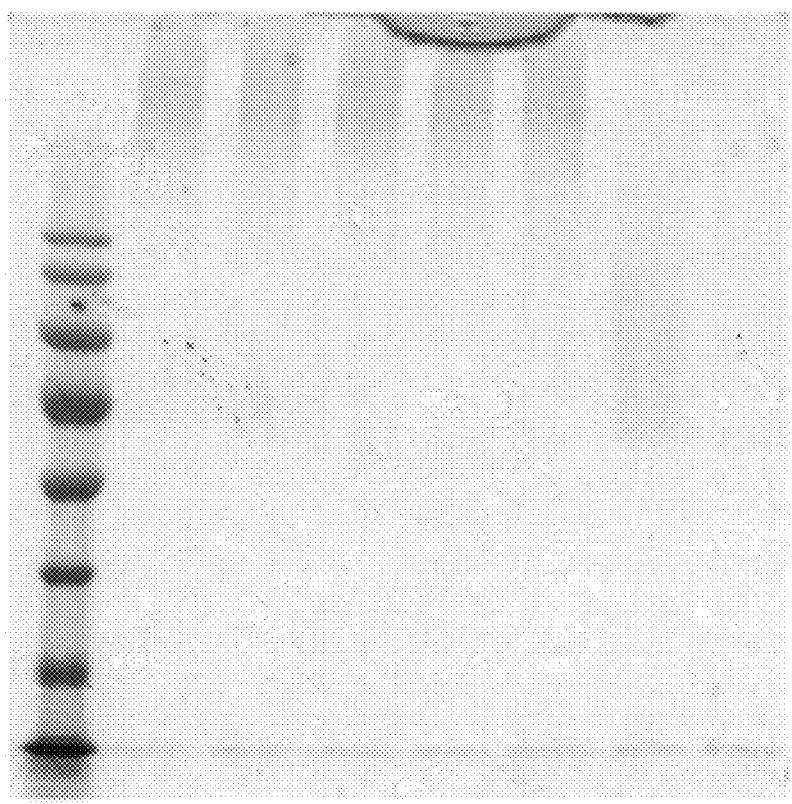

The full genome of phage 1611E-K2-1 was determined as 47,797 bp in length. Annotation of the genome sequences showed that this phage was predicted to contain 17 open reading frames (ORFs) of more than 500 bp. Analysis of the ORFs of phage 1611E-K2-1 revealed that predicted ORF16 exhibited 46% amino acid identity with a tailspike 63D sialidase, suggesting that the protein might correspond to a capsule depolymerase. The K2-orf16 gene was cloned and expressed in *E. coli*. The purity of purified recombinant K2-ORF16 protein was shown in FIG. 1(A). Upon spotting on a plate inoculated with *K. pneumoniae* 1611E, the recombinant K2-ORF16 protein generated a translucent spot resembling the plaque halo (FIG. 1(B)). The CPS were extracted from 1611E and then treated with K2-ORF16 protein were separated on the SDS-PAGE and stained with alcian blue (FIG. 1(C)). The results demonstrated that the K2-ORF16 protein could digest the K2 CPS. The sensitivity of this enzyme to capsular type K2 was further confirmed in another 7 capsular type K2 strains. The results suggested that the K2-ORF16 protein is a K2 capsule depolymerase.

Identification of the Putative K62 Capsule Depolymerase

A phage infecting strains with capsular types K10 and K62 was isolated from untreated water, denoted as phage Ref-K10-1. Two putative capsule depolymerases (ORF5 and ORF6) were identified from analysis of phage genome sequencing. After expression of these two proteins, ORF6 was demonstrated as K62 capsule depolymerase which can generate a translucent spot on the plate inoculated with K62 reference strain.

Example 3 Analysis of K1-ORF34 Capsule Depolymerase Digested CPS

Figure 2A:
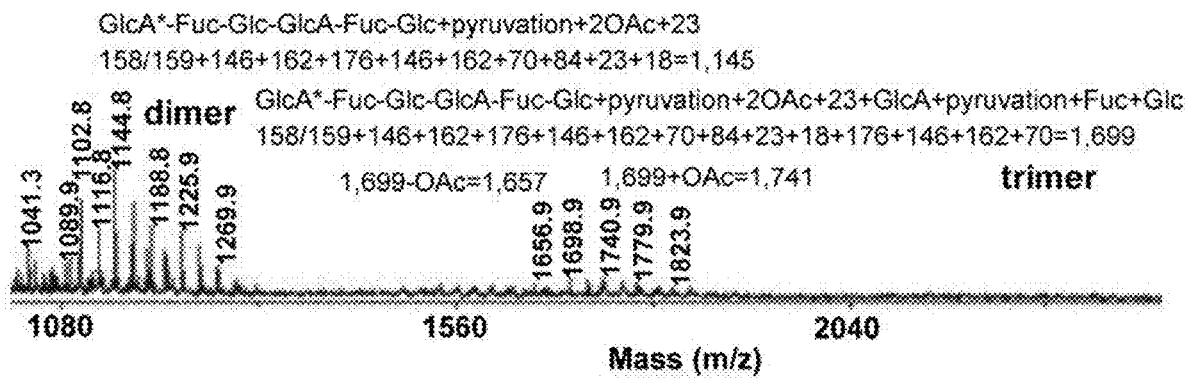
FIGS. 2 (A) to (D) show the mass and capillary electrophoresis analysis of K1 CPS digested by K1-ORF34 protein. (A) Mass distribution of K1 CPS cleaved by K1-ORF34 and Biogel P6 separation. (B) Capillary electrophoresis of K1 CPS cleaved by K1-ORF34 protein. (C) MS-MS spectra of K1 CPS fragment (MW 1,145). (D) $^1$H-NMR of K1-oligosaccharides.
Figure 2B:
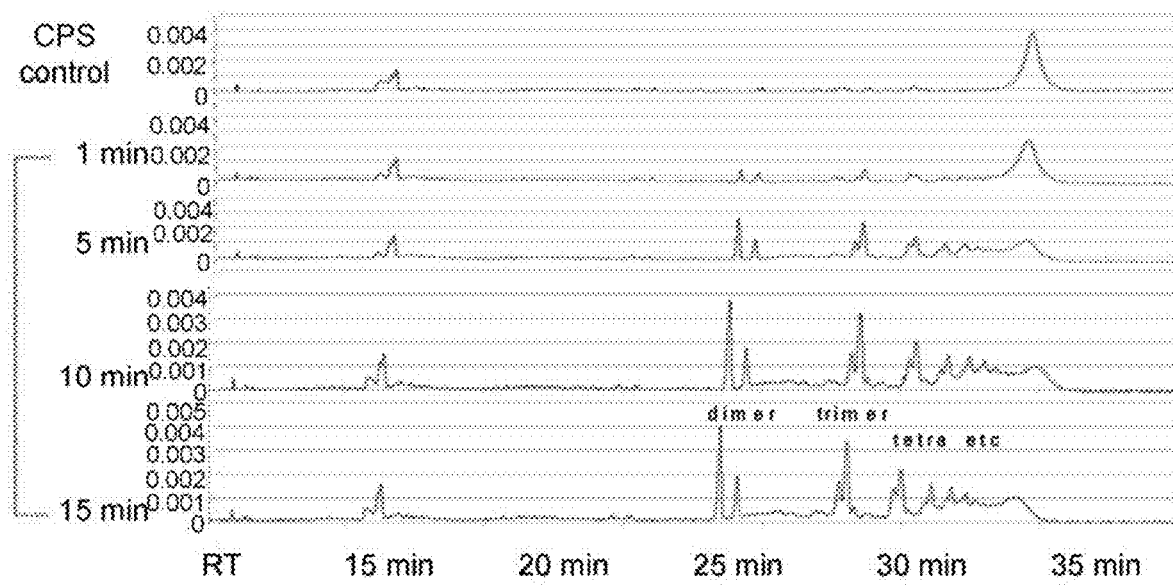
Figure 2C:
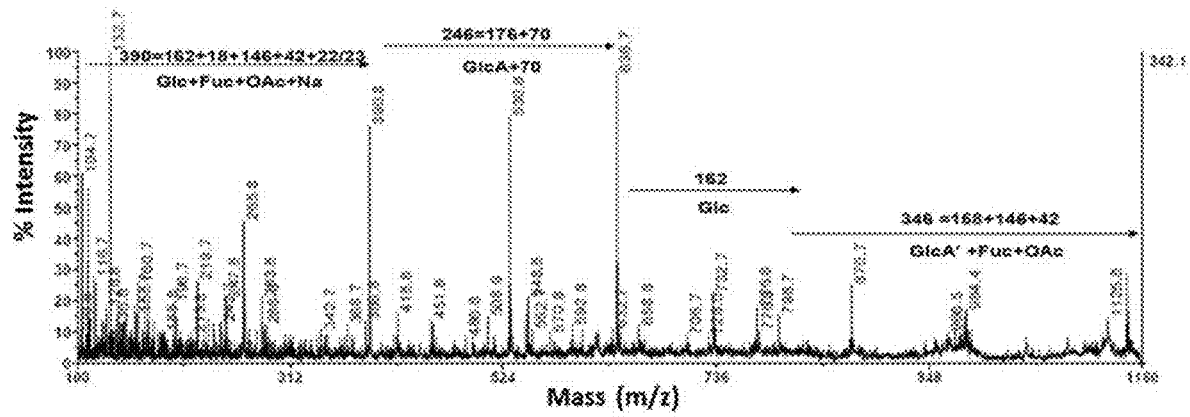
Figure 2D:
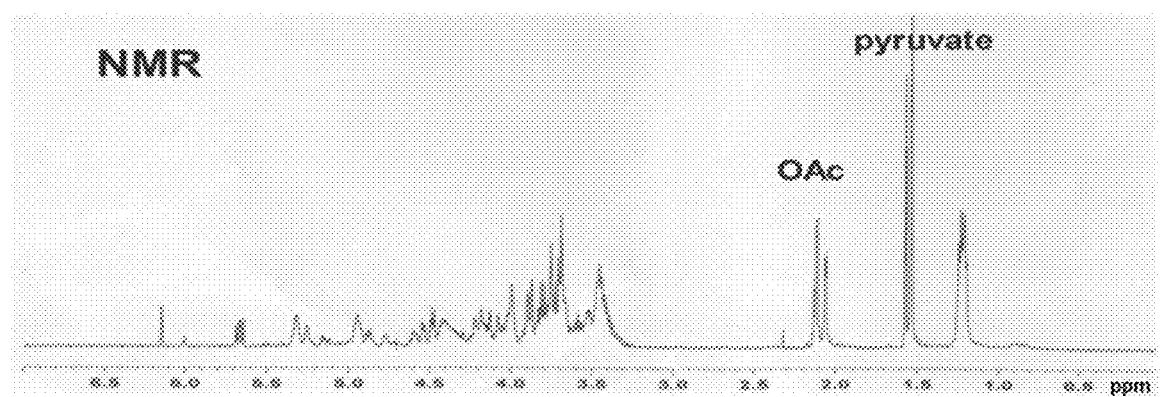

The structure of K1-ORF34 capsule depolymerase digested CPS was further analyzed. After incubation with purified K1-ORF34 protein, K1 CPS was reduced to oligosaccharides. Separation by size-exclusion chromatography and analysis by mass spectrum and capillary electrophoresis revealed that the majority of oligosaccharides were hexasaccharides, and ennea-saccharides were minor, that are dimers and trimers of trisaccharides unit (FIGS. 2(A) and (B)). From MS-MS analysis of the oligosaccharides with molecular weight in 1145, it showed that glucuronic acid was reduced into a double-bond derivate which was absorbed at 232 nm, and the modifications including pyruvation and acetylation were maintained (FIG. 2(C)). The structure of digested oligosaccharides was assayed by NMR spectra (FIG. 2(D)). The K1-ORF34 digested oligosaccharides still could be recognized by anti-K1 antisera (data not shown). Therefore, the K1-ORF34 enzyme belongs to one kind of lyases and could be applied for the development of K1 CPS conjugate vaccine.

Example 4 Analysis of Capsule Depolymerase Digested CPS

Analysis of K2-ORF16 Capsule Depolymerase Digested CPS

Figure 3A:
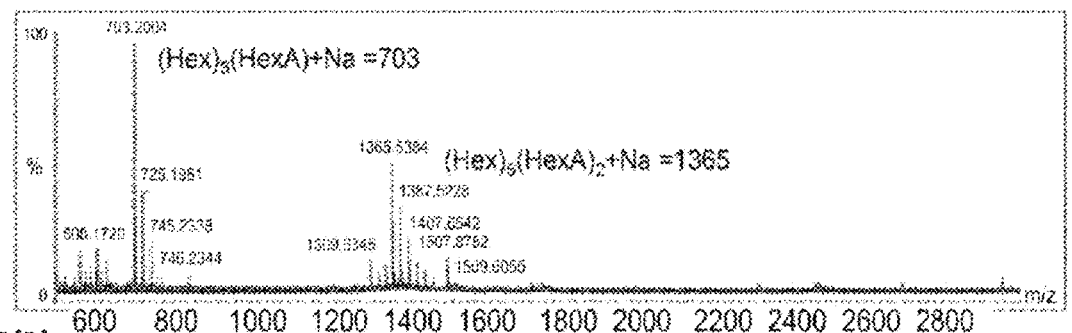
FIGS. 3 (A) to (C) show the structure analysis of K2 CPS digested by K2-ORF16 protein. (A) The MALDI-TOF spectra of K2 CPS digested by K2-ORF16 protein. (B) ESI-MS/MS analysis of m/z at 703 and (C) at 1365.
Figure 3B:
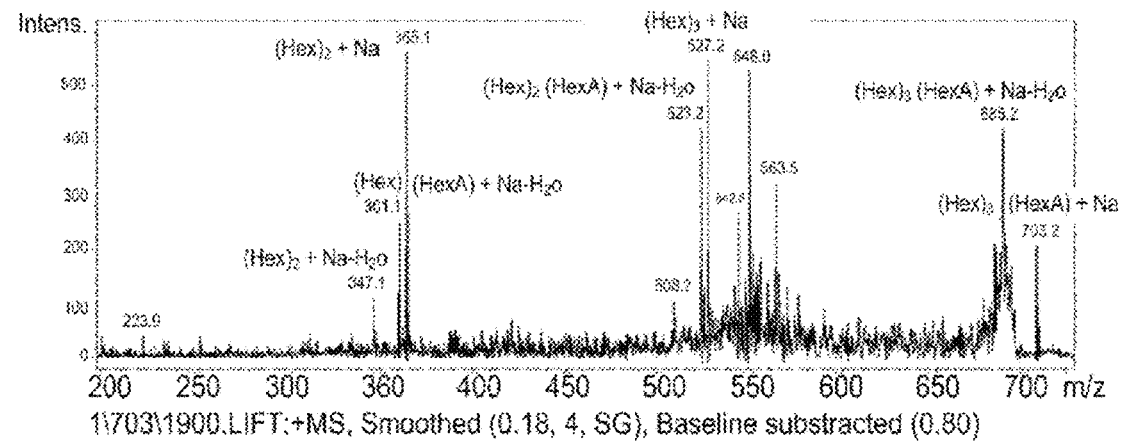
Figure 3C:
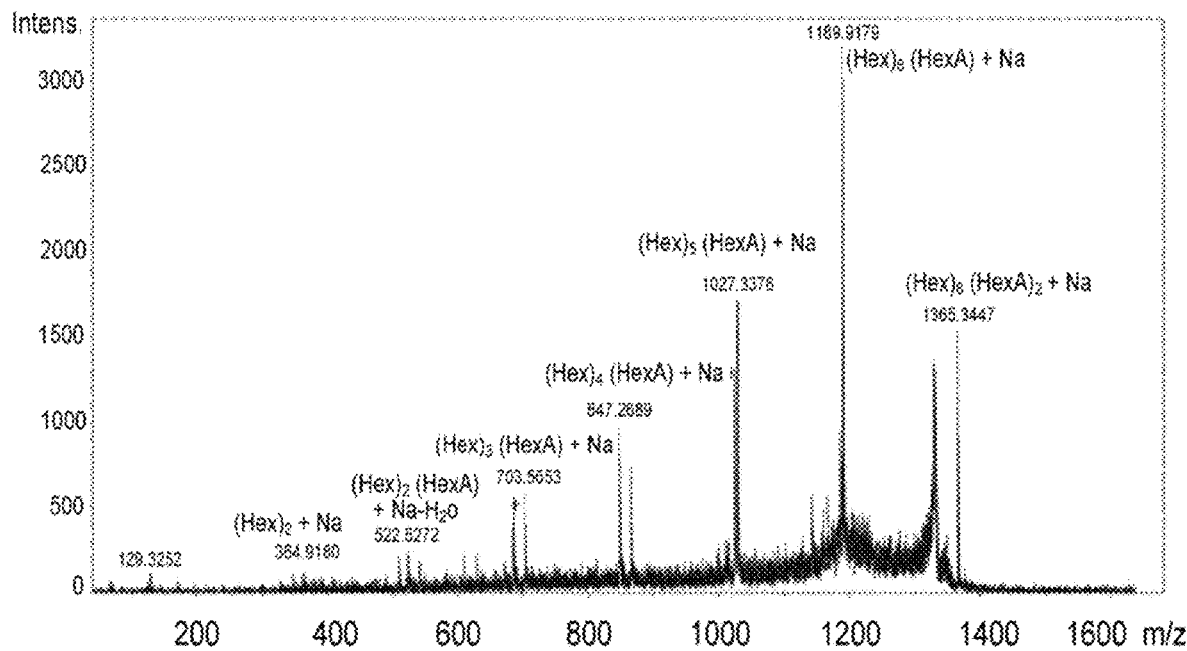

The structure of K2-ORF16 capsule depolymerase digested K2 CPS was further analyzed. After incubation with purified K2-ORF16 protein, K2 CPS was reduced to oligosaccharides. The spectra result indicated that two oligosaccharide components with different molecular weights (m/z of 703 and 1365) were released after the enzymatic degradation (FIG. 3(A)) and were further examined by ESI-MS/MS analysis (FIGS. 3(B) and (C)). Based on the structure of K2 CPS reported previously, the major products of K2-ORF16-digested CPS were tetrasaccharides (one repeat unit) and the minor products were octasaccharides (two repeat units). Therefore, the K2-ORF16 enzyme belongs to one kind of hydrolases and could be applied for the development of K2 CPS conjugate vaccine.

Analysis of K62 Capsule Depolymerase Digested CPS

Figure 4:
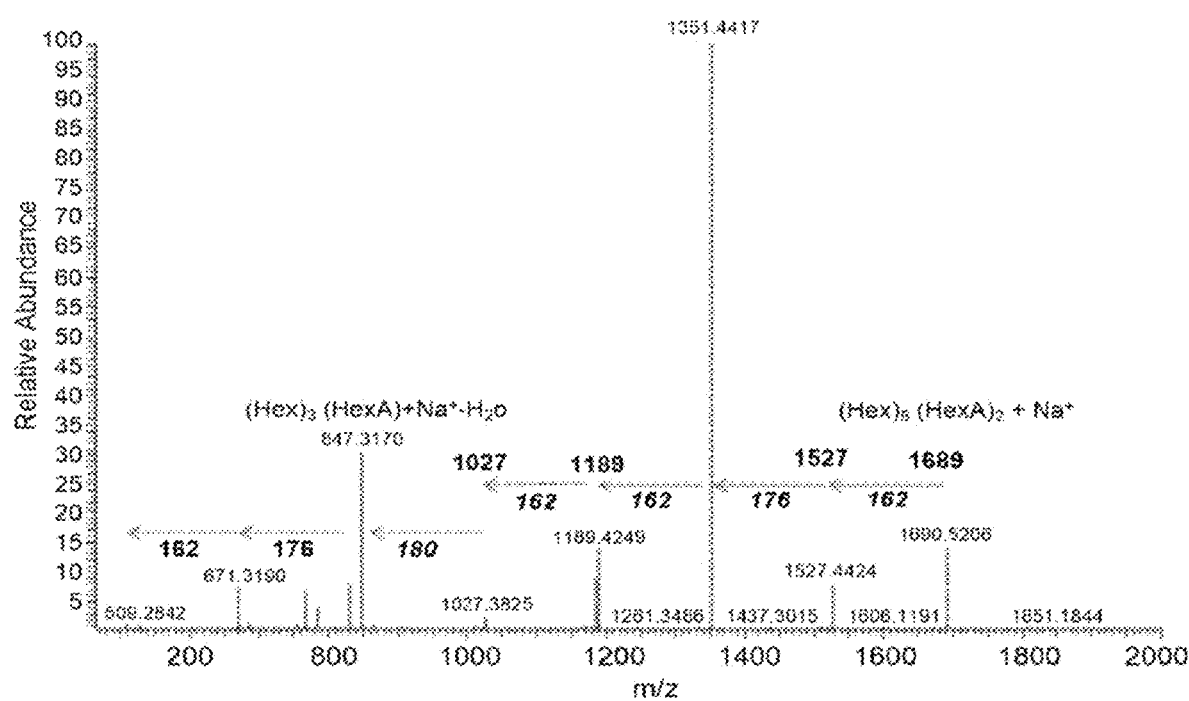
FIG. 4 shows the structure of major product of K62 capsule depolymerase-digested K62 CPS by Mass-Mass analysis.

The structure of K62 capsule depolymerase digested K62 CPS was further analyzed. After incubation with purified K62 capsule depolymerase, K62 CPS was reduced to oligosaccharides. From the results of MALDI-TOF and MS-MS spectra, the products of digested K62 CPS are two repeated units (decasaccharide) as majority and one repeat unit (pentasaccharide) as minority (FIG. 4). From mass analysis, the K62 capsule depolymerase belongs to one kind of hydrolases and could be applied for the development of K62 CPS conjugate vaccine.

The capsule depolymerase digested CPSs of KN2, K24, K28 and K64 were analyzed according to similar methods as mentioned above.

Example 5 CPS Conjugate Vaccines

The major sugar chain lengths of K1, K2, K24, K28, K62 and K64 oligosaccharides for conjugation with CRM197 carrier protein are as follows: hexasaccharide (two repeat units of K1 CPS), tetrasaccharide (one repeat unit of K2 CPS), decasaccharide (two repeat units of K62 CPS), hexasaccharide (one repeat unit of K64 CPS), pentasaccharide (one repeat unit of K24 CPS) and hexasaccharide (one repeat unit of K28 CPS). The epitope ratio was determined by MALDI-TOF mass spectrometry and the amount of glycan was calculated accordingly. As K1 as a representative example, by changing the amount of digested K1 CPS-SH we can have the immunogen ratio from 1:1.4 to 1:10.2; the detail immunogen ratio for K1 vaccine is shown in the table below. The immunogen ratio was determined by MALDI-TOF mass spectrometry.

|   | Ratio (CRM197:Sugar) | Amount of CRM197 (µg) | Amount of Sugar (µg) |
|---|---|---|---|
| 1 | 1:1.4 | 2299.5 | 62.1 |
| 2 | 1:3.0 | 1288.8 | 71.2 |
| 3 | 1:5.1 | 537.6 | 53.0 |
| 4 | 1:5.8 | 380.8 | 42.6 |
| 5 | 1:8.4 | 372.8 | 60.5 |
| 6 | 1:9.4 | 427.2 | 77.5 |
| 7 | 1:10.2 | 277.2 | 54.6 |

Example 6 Toxicology Assay (K1 as a Representative Example)

Figure 5A:
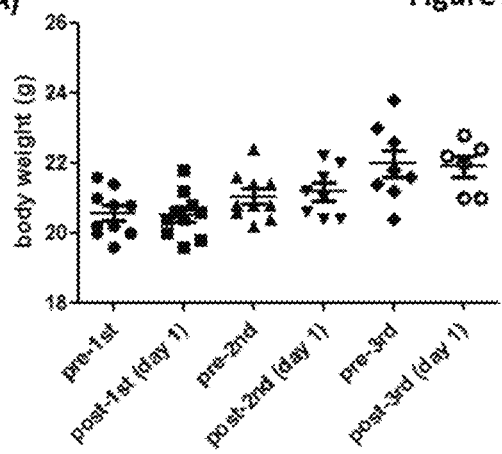
FIGS. 5 (A) to (C) show the safety of K1 CPS conjugated vaccine. (A) The body weights of mice before and one day after each administration of K1 CPS conjugate vaccine were recorded. (B) The rectal temperatures of mice before and one day after each administration of K1 CPS conjugate vaccine were recorded. (C) The liver (ALT) and renal (BUN and creatinine) functions of mice one week after each administration of K1 CPS conjugate vaccine were determined.
Figure 5B:
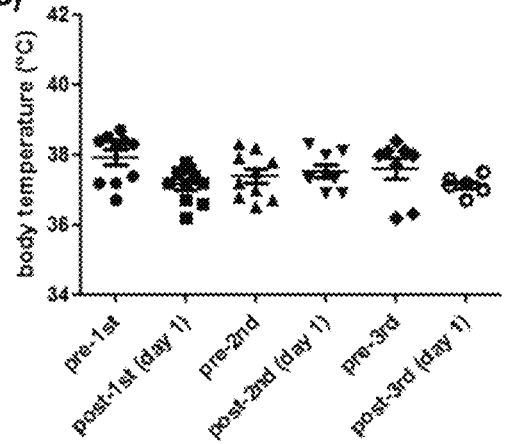
Figure 5C:
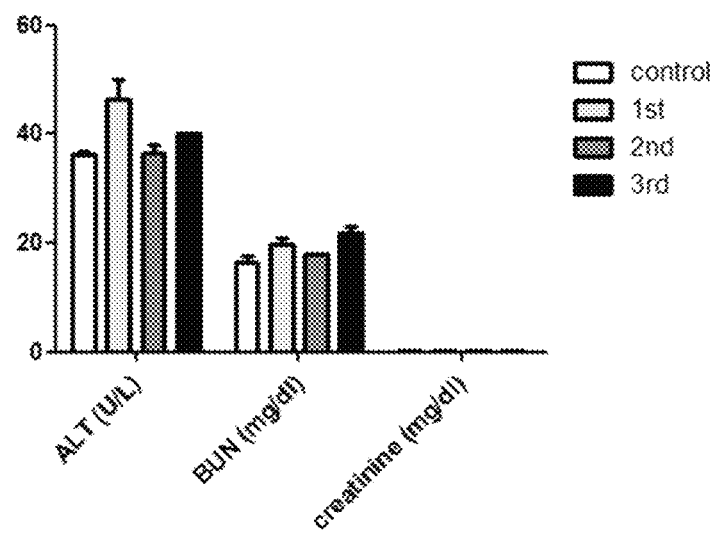

The body weights (FIG. 5(A)) and rectal temperatures (FIG. 5(B)) of mice before and one day after each vaccination of K1 CPS conjugated vaccine were recorded. Sera of mice were collected at one week after $1^{st}$, $2^{nd}$ and $3^{rd}$ administration of K1 CPS conjugate vaccines and then the liver (ALT) and renal (BUN and creatinine) functions were determined (FIG. 5(C)). These results indicated that side effects were not observed in mice administrated with three doses of K1 CPS conjugate vaccine. The toxicology assays for the CPS of K2, K24, K28, K62 or K64 was conducted according to similar method as mentioned above.

Example 7 Antibody Response and Serum Bactericidal Assay

Figure 6:
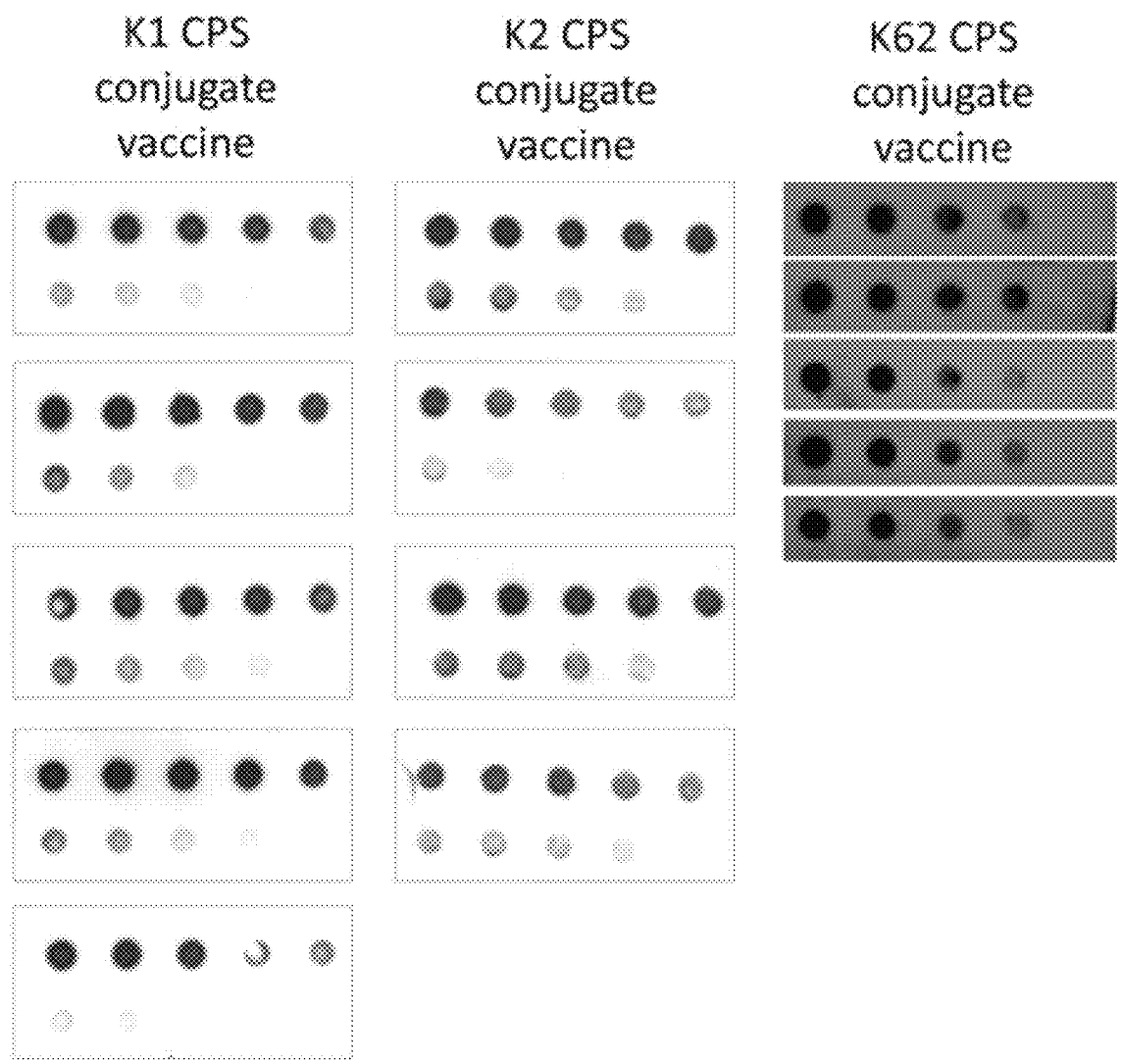
FIG. 6 shows the inductions of antibodies against CPS in mice received the K1 or K2 or K62 CPS conjugate vaccine. The different amounts of K1 or K2 (2000 ng to 7.8125 ng, two-fold dilution) or K62 CPS (4000 ng to 500 ng, two-fold dilution) transferred onto membrane were blotted with sera (1:1000 dilution) from mice received K1 or K2 or K62 CPS conjugate vaccine.

Sera of mice IM administrated with K1 or K2 or K62 CPS conjugated vaccine collected for antibody detection and bactericidal assay. The results of dot blotting indicated that antibodies induced by the CPS conjugated vaccines can interact with their original CPS (FIG. 6).

The results of bactericidal assay revealed that sera from K1 CPS conjugated vaccine immunized mice can kill more than 50% K1 bacteria compared to the sera from non-immunized mice even a 1:128 dilution of sera was used (the bactericidal titer was 32 to 128). The bactericidal titer to K2 bacteria of sera from mice immunized with K2 CPS conjugated vaccine was 8 to 32. The bactericidal activity to K62 bacteria was detected in 40% sera from mice immunized with K62 CPS conjugated vaccine (the bactericidal titer was 8 to 32). Therefore, the CPS conjugated vaccine can successfully induce production of capsular type specific antibody in mice and the antibody has bactericidal effect.

Example 8 Protection Assay

Figure 7A:
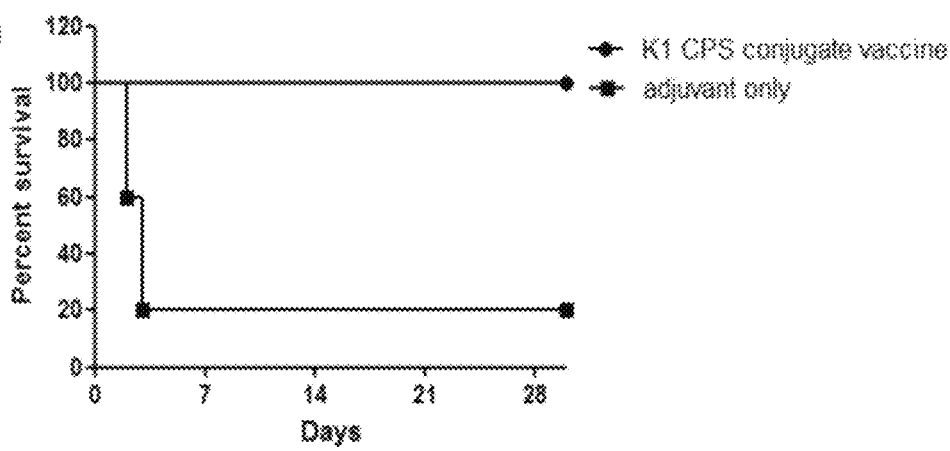
FIGS. 7 (A) to (C) show the efficacies of the K1 or K2 or K62 CPS conjugate vaccine in mice. Five mice immunized with K1 or K2 CPS conjugate vaccine were IP inoculated with $1\times10^4$ CFU of *K. pneumoniae* NTUH-K2044 (A) or NTUH-A4528 (B), respectively. Vaccination with K1 or K2 CPS conjugate vaccine significantly increased the survival of mice infected with *K. pneumoniae* NTUH-K2044 (P=0.0144, log-rank test) or NTUH-A4528 (P=0.0023, log-rank test). Five mice inoculated with the K62 CPS conjugated vaccine which were treated with cyclophosphamide to induce neutropenia were then challenged with $5\times10^6$ cfu of K62 bacteria (C). K62 CPS conjugated vaccine significantly protect immunocompromised mice from subsequent infection of K62 bacteria (P=0.0448, log-rank test).
Figure 7B:
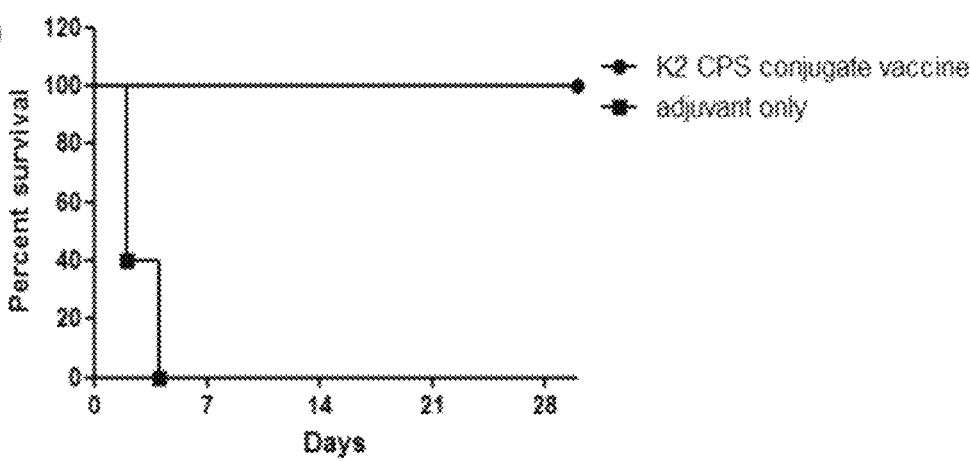

The immunized mice were also challenged with *K. pneumoniae* to evaluate if the vaccine has protective effect in vivo. Mice were IM inoculated with K1 or K2 CPS conjugated vaccine once a week (the control group were given adjuvant only). One week after third vaccination, mice were IP infected with $1 \times 10^4$ CFU *K. pneumoniae* NTUH-K2044 or NTUH-A4528. The result of the 30 days after challenging with *K. pneumoniae* revealed that the survival rate of mice received K1 or K2 CPS conjugated vaccine was significantly higher than those that had received adjuvant only (FIGS. 7(A) and (B)).

Figure 7C:
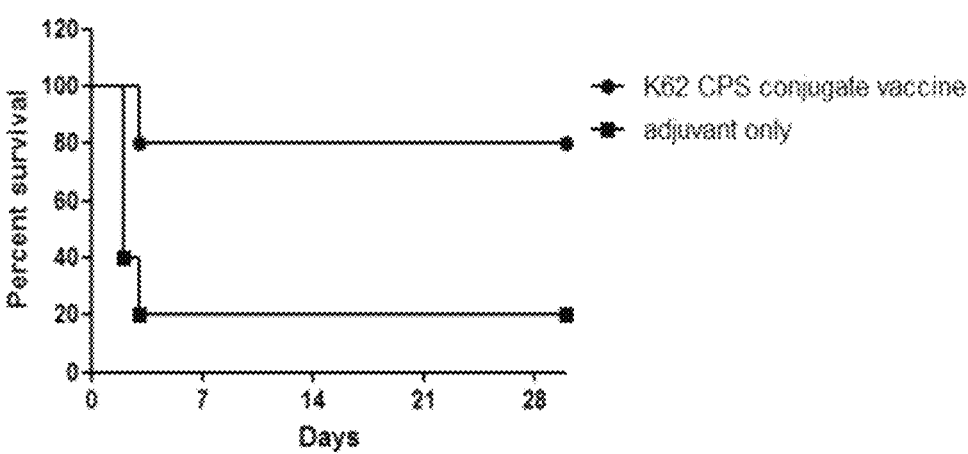

Mice inoculated with the K62 CPS conjugated vaccine which were treated with cyclophosphamide to induce neutropenia were then challenged with $5 \times 10^6$ cfu of K62 bacteria. K62 CPS conjugated vaccine significantly protect immunocompromised mice from subsequent infection of K62 bacteria (FIG. 7(C)).

Example 9 Efficacy of K1 and K2 CPS Conjugated Divalent Vaccines

Figure 8A:
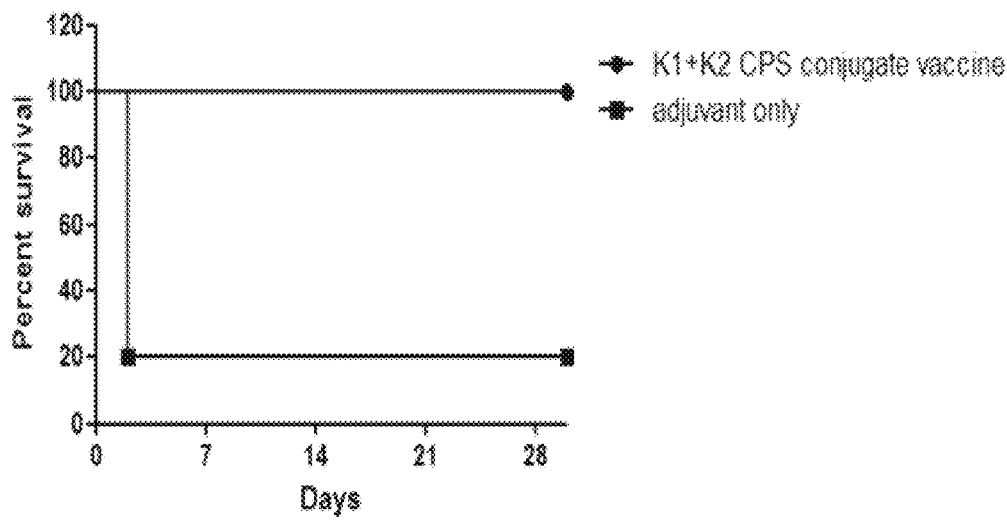
FIGS. 8 (A) and (B) show the efficacy of the K1 and K2 CPS conjugate divalent vaccine in mice. Five mice immunized with K1 and K2 CPS conjugate divalent vaccine were IP inoculated with $1\times10^4$ CFU of *K. pneumoniae* NTUH-K2044 (A) or NTUH-A4528 (B), respectively. Vaccination with K1 and K2 CPS conjugate divalent vaccine significantly increased the survival of mice infected with *K. pneumoniae* NTUH-K2044 (P=0.0143, log-rank test) or NTUH-A4528 (P=0.0023, log-rank test).
Figure 8B:
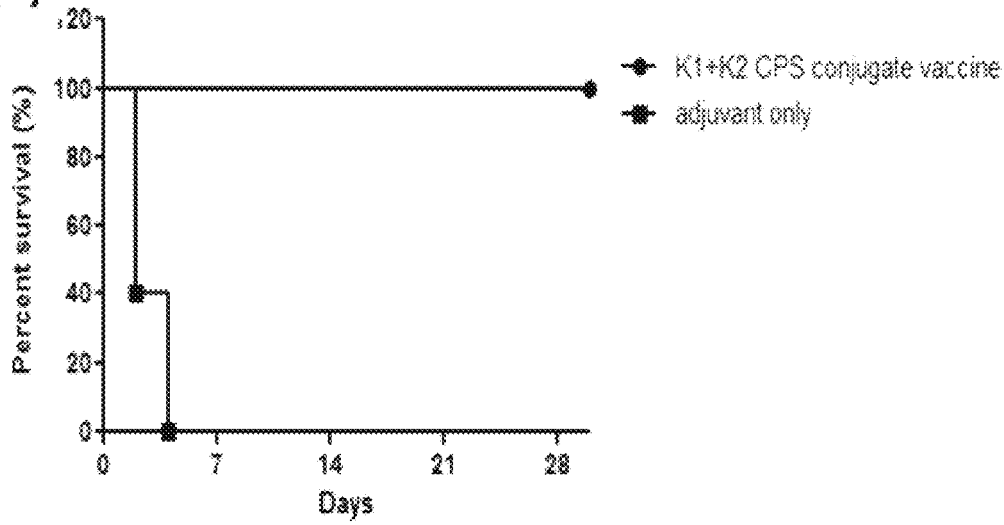

K1 and K2 are the prevalent capsular types of *K. pneumoniae* strains causing invasive infections. Therefore, the protection efficacy of divalent vaccine (mixtures of equal amounts of K1 and K2 CPS conjugated vaccines) was further examined (FIGS. 8(A) and (B)). IP infection with $1 \times 10^4$ CFU of NTUH-K2044 and NTUH-A4528 resulted in 80% and 100% death of adjuvant-received mice, respectively. In contrast, no mortality was observed among divalent vaccine-received mice after IP infection. Thus, divalent vaccination significantly protected the mice from the infection of K1 and K2 *K. pneumoniae* simultaneously.

Example 10 the Structures of K64, K24, K28 and KN2 Capsule Depolymerase Digested CPS

1. K64

Figure 9:
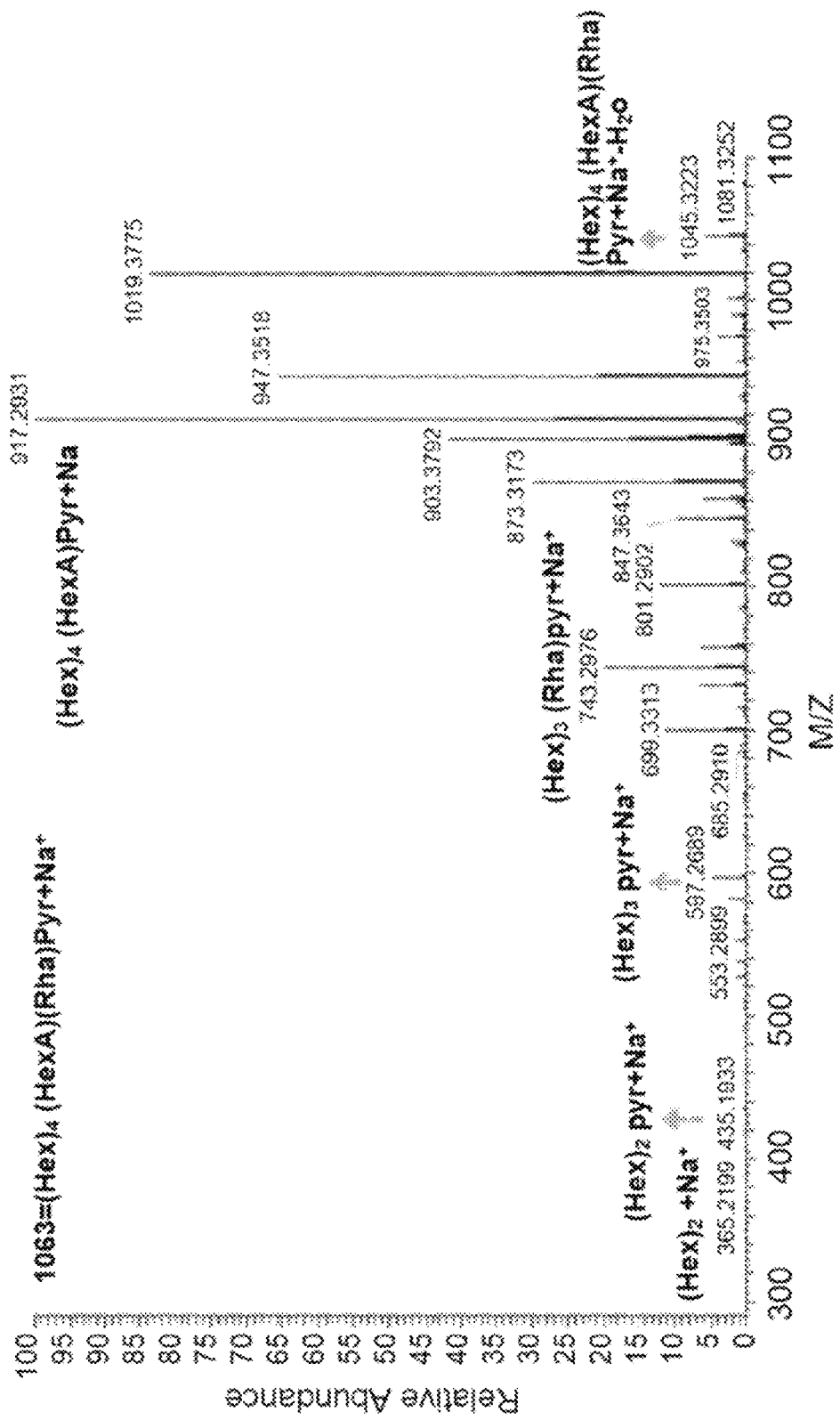
FIGS. 9 to 12 show the spectrum of K64 CPS, K24 CPS, K28 CPS and KN2 CPS, respectively.

Digested K64 CPS are major in one repeat unit (hexasaccharide) and minor in two repeats (dodecasaccharides). The K64 CPS-cleavage enzyme is to be one kind of lyases because the new double bond signal is shown in the NMR spectra of the reaction products. The major K64 fragment MS-MS (Hexasaccharide) is shown in FIG. 9.

2. K24

Figure 10:
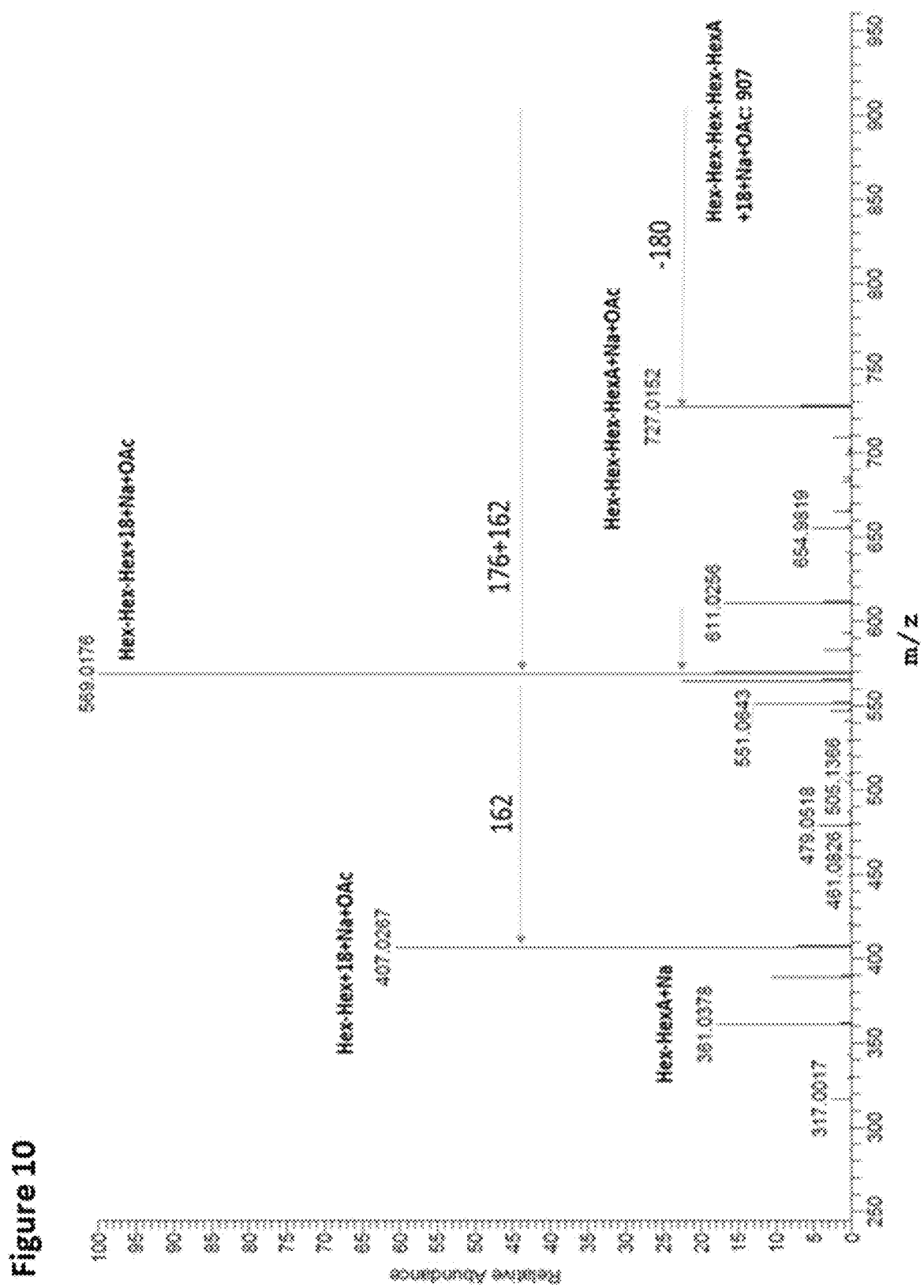

According to the published K24 CPS structure, it was composed of four hexoses and one hexuronic acid. The spectrum of digested K24 CPS showed that the major product was two-repeat unit oligosaccharide with acetylation modification [m/z 1773, $(Hex)_8(HexA)_2$], and the minor one was one-repeat unit oligosaccharide with/without acetylation modification (m/z 907 and 865), indicating that K24 enzyme works as one kind of hydrolase. The major K24 fragment MS-MS (Pentasaccharide) is shown in FIG. 10.

3. K28

Figure 11:
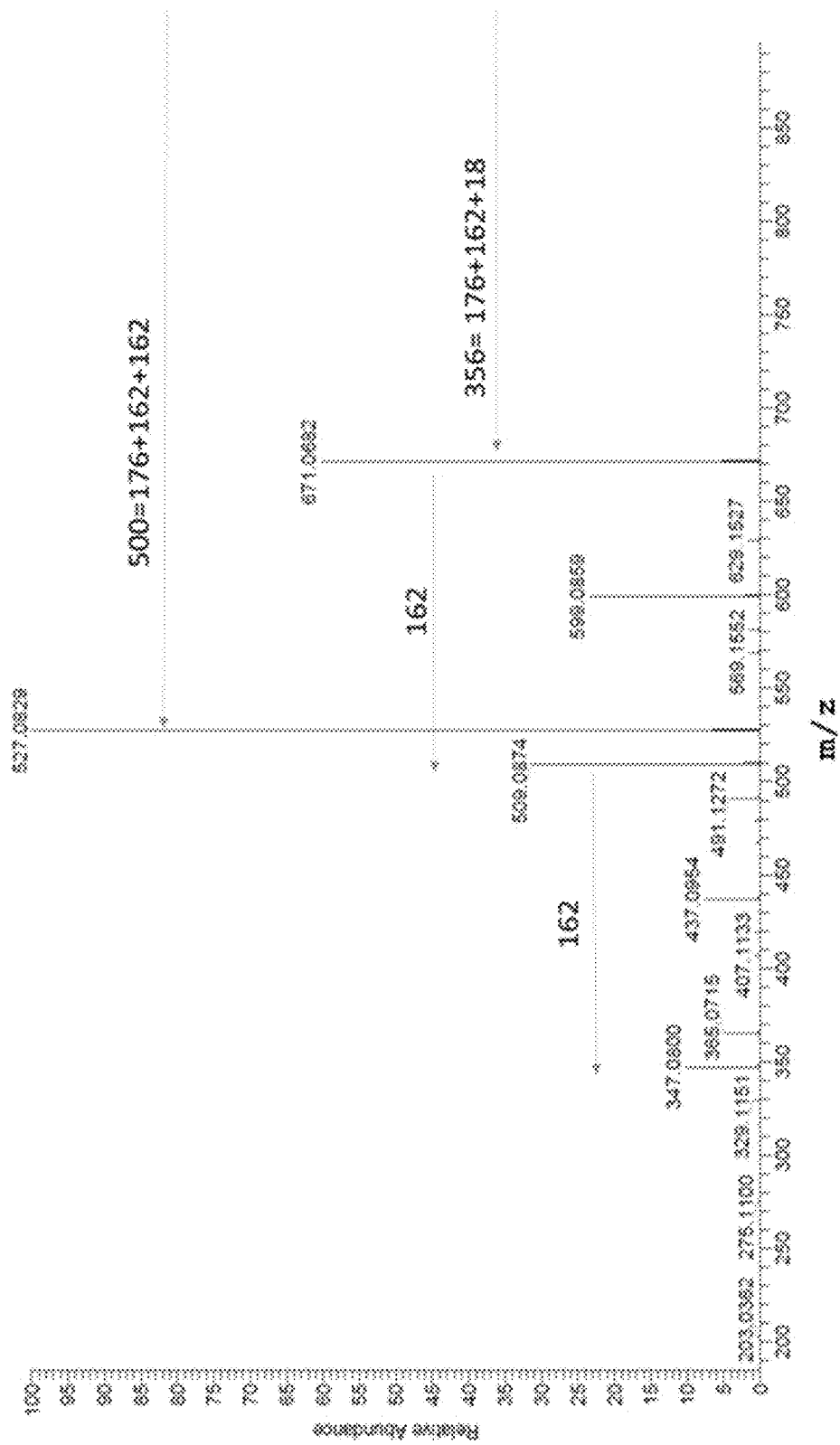

From the spectrum of MALDI-TOF, it showed that the digest-KN2 CPS is major in one repeat unit (hexasaccharide). The major K28 fragment MS-MS (Hexasaccharide) is shown in FIG. 11.

4. KN2

Figure 12:
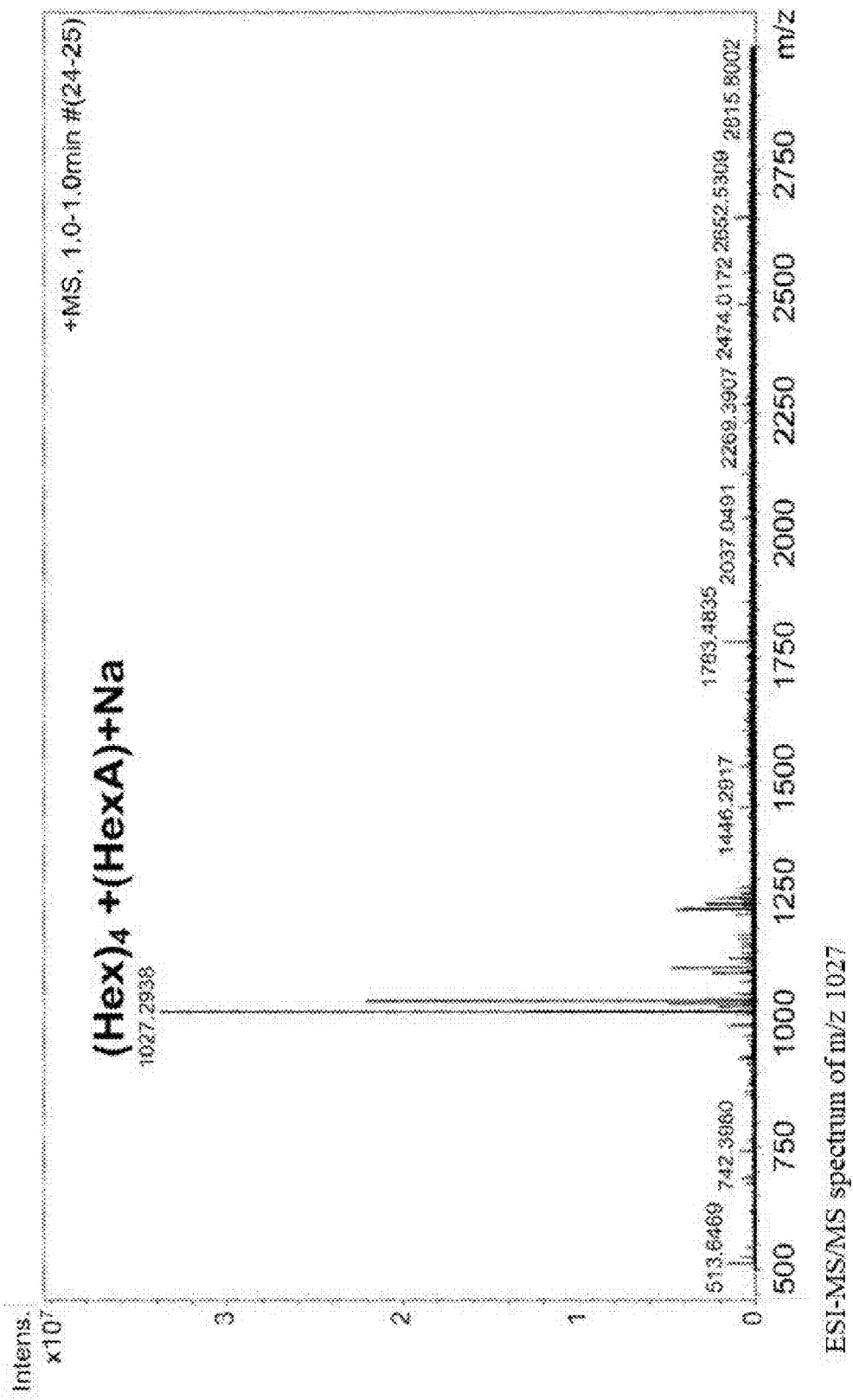
Figure 12:
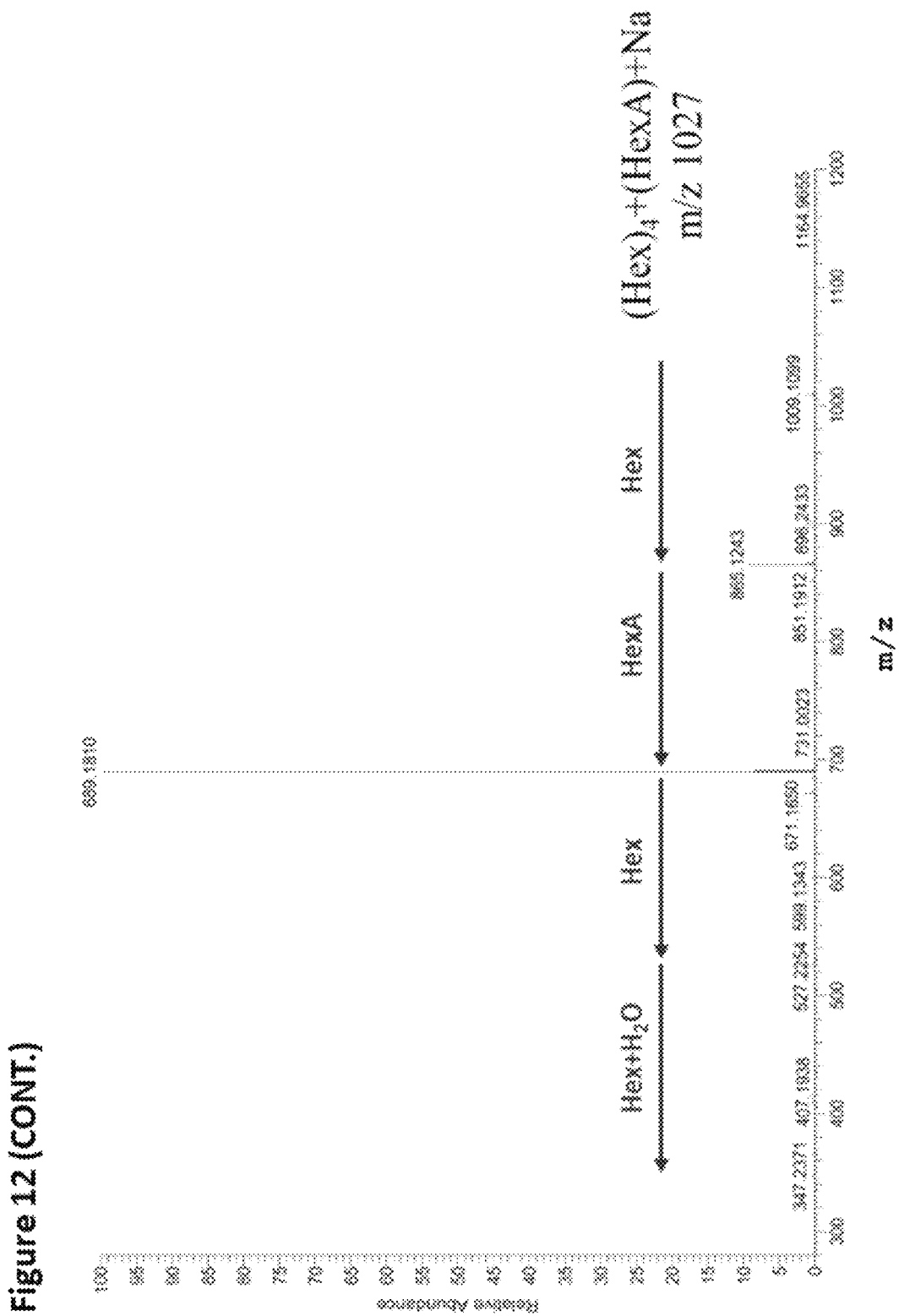

*K. pneumoniae* KN2 belongs to a new capsular type, there was still no publication describing its chemical structure. From the spectrum of MALDI-TOF, it showed that the digest-KN2 CPS is composed of four hexoses and one hexuronic acid (MW 1027). Further, the KN2 enzyme was one kind of hydrolases according to the m/z value of the MALDI-TOF. The m/z 1027 was further analyzed by ESI-MS/MS. The fragments of the MS/MS spectrum confirmed that our speculation was correct. In the near future, the composition and linkages of KN2 CPS by GC-MS will be applied to elucidate the detail chemical structure of KN2 CPS. The MALDI-TOF spectrum of KN2 hydrolase-digested CPS is shown in FIG. 12.

Example 11 Comparison Between CPS Vaccine and CPS Conjugated Vaccine

The induction of anti-CPS antibodies and serum bactericidal activity in mice received K1 crude CPS (2 µg) or K1

Figure 13:
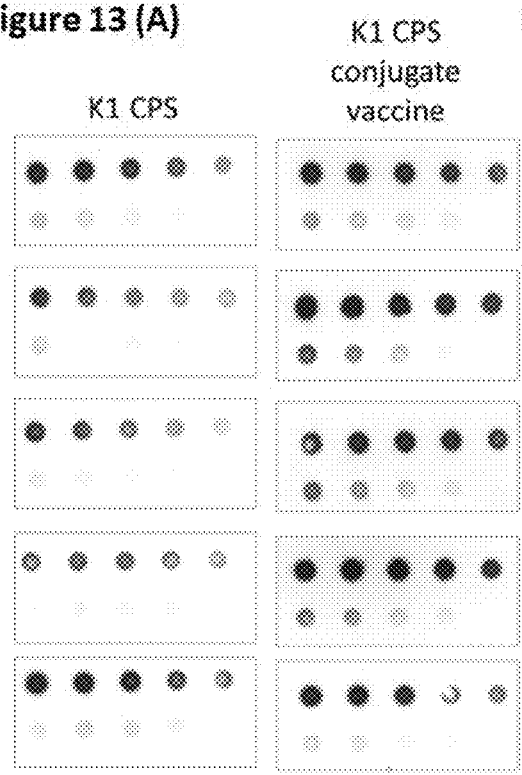
FIGS. 13 (A) and (B) show the inductions of antibodies against K1 CPS (A) and serum bactericidal activity (B) in mice received the K1 crude CPS or K1 CPS conjugated vaccine. The different amounts of K1 (2000 ng to 7.8125 ng, two-fold dilution) transferred onto membrane were blotted with sera (1:1000 dilution) from five mice received K1 crude CPS or K1 CPS conjugated vaccine.
Figure 13:
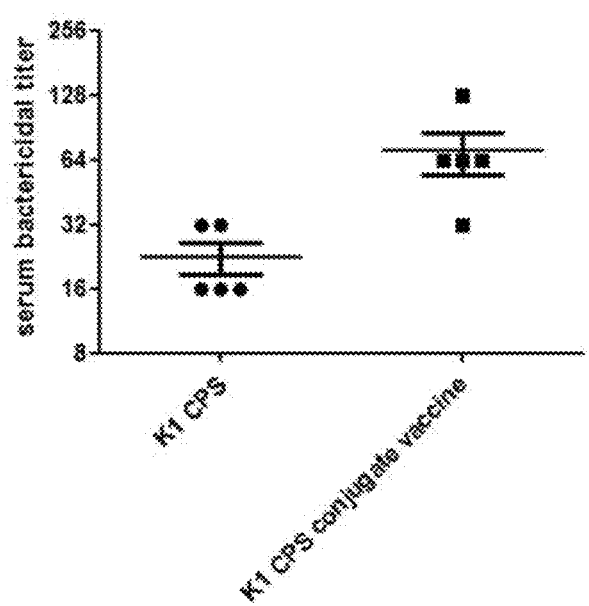

CPS conjugated vaccine (2 μg) were compared (FIGS. 13 (A) and (B)). The amounts of anti-K1 antibodies in mice received K1 CPS conjugated vaccine were higher than those in mice received K1 crude CPS. Accordingly, the serum bactericidal activity was also significantly higher in mice received K1 CPS conjugated vaccine.

---

What is claimed is:

1. An immunogen comprising a repeat unit of trisaccharide of *Klebsiella pneumoniae* K1 capsular polysaccharide (CPS), which has the following Formula (I):

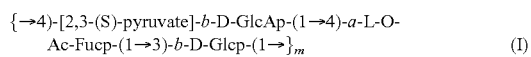

$$\{\rightarrow 4)\text{-}[2,3\text{-}(S)\text{-pyruvate}]\text{-}b\text{-D-GlcAp-}(1\rightarrow 4)\text{-}a\text{-L-O-Ac-Fucp-}(1\rightarrow 3)\text{-}b\text{-D-Glcp-}(1\rightarrow\}_m \quad (I)$$

wherein m is 1 to 4; and wherein the Formula (I) is linked to a terminal group consisting of thiol (—SH) at reducing end of the repeat unit.

2. The immunogen of claim 1, wherein m is 2.

3. An immunogen comprising a repeat unit of tetrasaccharide of *Klebsiella pneumoniae* K2 CPS, which has the following Formula (II):

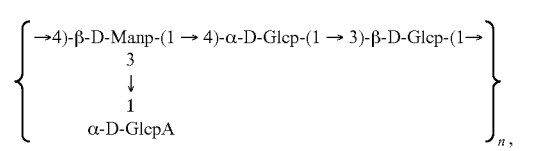

wherein n is 1 to 4; and wherein the Formula (II) is linked to a terminal group consisting of thiol (—SH) at reducing end of the repeat unit.

4. The immunogen of claim 3, wherein the K2 CPS contains one repeat unit (n=1).

5. An immunogen comprising a repeat unit of hexasaccharide of *Klebsiella pneumoniae* K64 CPS, which has the following Formula (III):

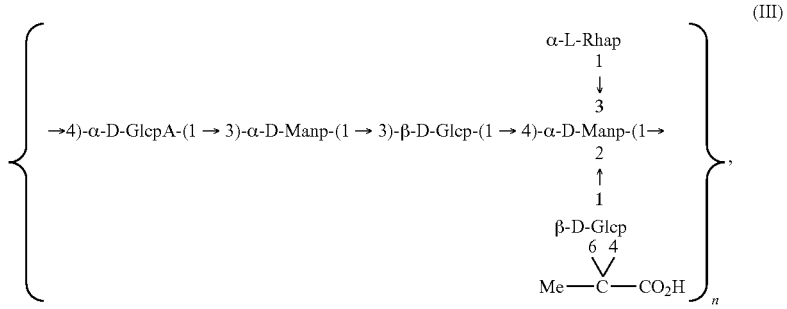

wherein n is 1 to 4, and wherein the Formula (III) is linked to a tell final group consisting of thiol (—SH) at reducing end of the repeat unit.

6. The immunogen of claim 5, wherein n is 1.

7. An immunogen comprising a repeat unit of pentasaccharide of *Klebsiella pneumoniae* K62 CPS, which has the following Formula (IV):

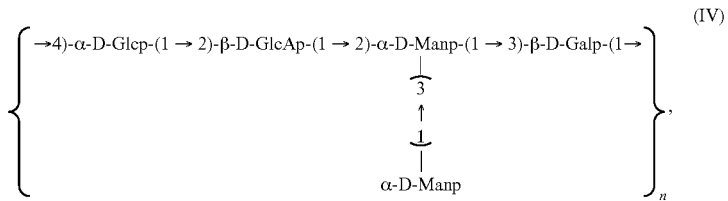

wherein n is 1 to 4, and wherein the Formula (IV) is linked to a tell final group consisting of thiol (—SH) at reducing end of the repeat unit.

8. The immunogen of claim 7, wherein n is 2.

9. An immunogen comprising a repeat unit of pentasaccharide of *Klebsiella pneumoniae* K24 CPS, which has the following Formula (V):

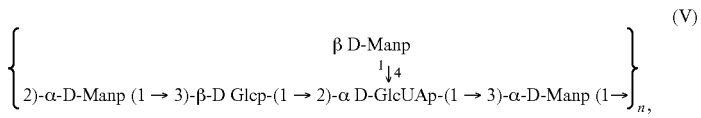

wherein n is 1 to 4; and wherein the Formula (V) is linked to a terminal group consisting of thiol (—SH) at reducing end of the repeat unit.

10. The immunogen of claim 9, wherein n is 1.

11. An immunogen comprising a repeat unit of hexasaccharide of *Klebsiella pneumoniae* K28 CPS, which has the following Formula (VI):

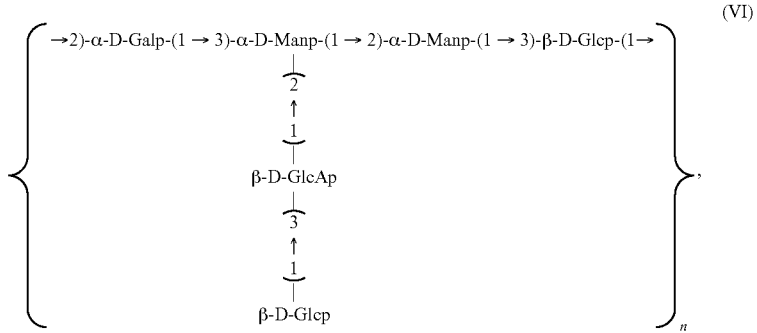

wherein n is 1 to 4; and wherein the Formula (VI) is linked to a terminal group consisting of thiol (—SH) at reducing end of the repeat unit.

12. The immunogen of claim 11, wherein n is 1.

13. An immunogen comprising a repeat unit of hexasaccharide of *Klebsiella pneumoniae* KN2 CPS, which has four hexoses and one hexuronic acid and about a molecule weight of about 1027; wherein the KN2 CPS is linked to a terminal group consisting of thiol (—SH) at reducing end of the repeat unit.

14. A vaccine comprising one or more immunogens comprising one or more digested *Klebsiella pneumoniae* capsular polysaccharides (CPS) selected from Formula (I) to (VI):

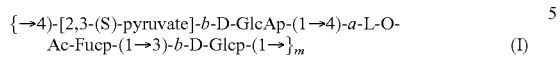
(I)

wherein Formula (I) belongs to capsular type K1 and m is 1 to 4;

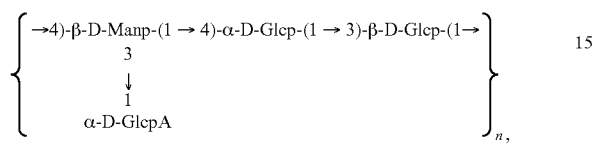
(II)

wherein Formula (II) belongs to capsular type K2 and n is 1 to 4;

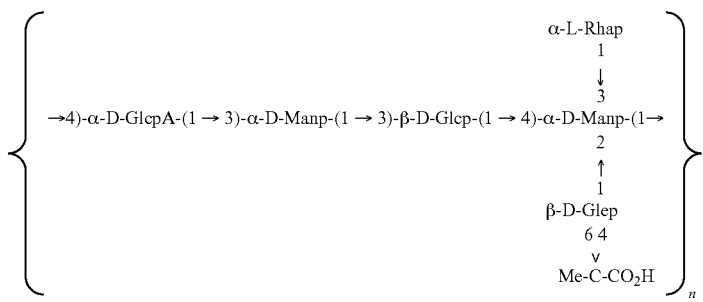
(III)

wherein Formula (III) belongs to capsular type K64 and n is 1 to 4;

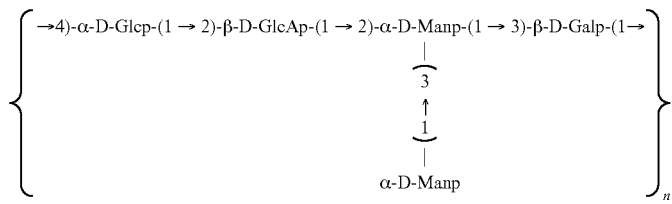
(IV)

wherein Formula (IV) belongs to capsular type K62 and n is 1 to

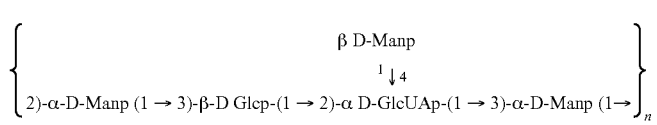
(V)

wherein Formula (V) belongs to capsular type K24 and n is 1 to 4; and

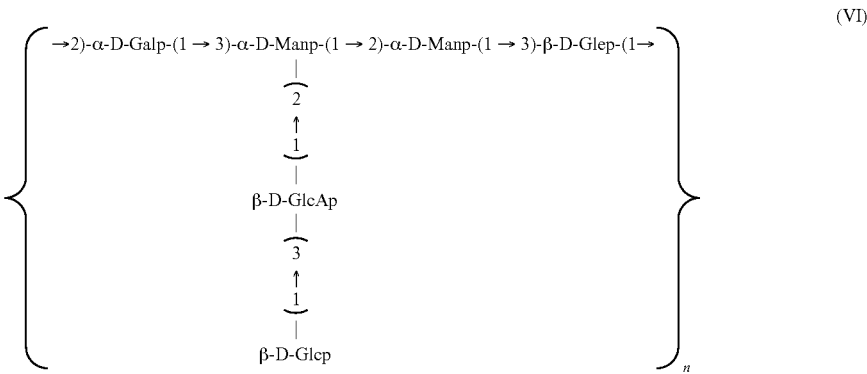

(VI)

wherein Formula (VI) belongs to capsular type K28 and n is 1 to 4;

wherein each of the Formula (I) to (VI) is linked to a terminal group consisting of thiol (—SH) at reducing end of the CPS.

15. The vaccine of claim 14, wherein the immunogen is conjugated with a carrier.

16. The vaccine of claim 14, wherein the vaccine is a K1 and K2 CPS-conjugated divalent vaccine comprising immunogens of Formula (I) and Formula (II).

17. The vaccine of claim 14, wherein the vaccine is a K1 and K2 CPS-conjugated divalent vaccine comprising a mixture of immunogen I-carrier and immunogen II-carrier, wherein the immunogen I having Formula (I) and the immunogen II having Formula (II) are conjugated with a carrier, respectively.

18. The vaccine of claim 14, wherein the vaccine is a K64 and K62 CPS-conjugated divalent vaccine comprising immunogens of Formula (III) and Formula (IV).

19. The vaccine of claim 14, wherein the vaccine is a K64 and K62 CPS-conjugated divalent vaccine comprising a mixture of immunogen III-carrier and immunogen IV-carrier, wherein the immunogen III having Formula (III) and the immunogen IV having Formula (IV) are conjugated with a carrier, respectively.

20. The vaccine of claim 15, 17 or 19, wherein the carrier is a protein, a peptide, a lipid, a polymer, a dendrimer, a virosome, a virus-like particle (VLP), or combinations of distinct carriers thereof.

21. The vaccine of claim 15, 17 or 19, wherein the carrier is a protein carrier.

22. The vaccine of claim 21, wherein the protein carrier is selected from the group consisting of a bacterial toxoid, a toxin, an exotoxin, and a nontoxic derivative thereof.

23. The vaccine of claim 21, wherein the protein carrier is CRM197 having an amino acid sequence as shown in SEQ ID NO:3.

24. A method of eliciting an immune response against a Klebsiella pneumoniae, comprising administering an effective amount of the immunogen of any one of claims 1 to 13 or a vaccine of any one of claims 14 to 23 to a subject.

25. A method of preventing infection of Klebsiella pneumoniae, comprising administering an effective amount of the immunogen of any one of claims 1 to 13 or a vaccine of any one of claims 14 to 23 to a subject.

26. The vaccine of claim 21, wherein the protein carrier is selected from the group consisting of keyhole limpet hemocyanine (KLH), hepatitis B virus core protein, thyroglobulin, albumins, bovine serum albumin (BSA), human serum albumin (HSA), ovalbumin, pneumococcal surface protein A (PspA), pneumococcal adhesin protein (PsaA), purified protein derivative of tuberculin (PPD), transferrin binding proteins, polyamino acids comprising poly(lysine: glutamic acid), tetanus toxoid, tetanus toxin Fragment C, diphtheria toxoid, CRM (a nontoxic diphtheria toxin mutant), cholera toxoid, Staphylococcus aureus exotoxins or toxoids, Escherichia coli heat labile enterotoxin, Pseudomonas aeruginosa exotoxin A, bacterial outer membrane proteins comprising Neisseria meningitidis serotype B outer membrane protein complex (OMPC) and outer membrane class 3 porin (rPorB).

* * * * *

SEQUENCE LISTING

<160> NUMBER OF SEQ ID NOS: 7

<210> SEQ ID NO 1
<211> LENGTH: 651
<212> TYPE: PRT
<213> ORGANISM: K1 specific phage

<400> SEQUENCE: 1

```
Met Ala Leu Ile Arg Leu Val Ala Pro Glu Arg Val Phe Ser Asp Leu
1               5                  10                  15

Ala Ser Met Val Ala Tyr Pro Asn Phe Gln Val Gln Asp Lys Ile Thr
            20                  25                  30

Leu Leu Gly Ser Ala Gly Gly Asp Phe Thr Phe Thr Thr Ala Ser
        35                  40                  45

Val Val Asp Asn Gly Thr Val Phe Ala Val Pro Gly Gly Tyr Leu Leu
    50                  55                  60

Arg Lys Phe Val Gly Pro Ala Tyr Ser Ser Trp Phe Ser Asn Trp Thr
65                  70                  75                  80

Gly Ile Val Thr Phe Met Ser Ala Pro Asn Arg His Leu Val Val Asp
                85                  90                  95

Thr Val Leu Gln Ala Thr Ser Val Leu Asn Ile Lys Ser Asn Ser Thr
            100                 105                 110

Leu Glu Phe Thr Asp Thr Gly Arg Ile Leu Pro Asp Ala Ala Val Ala
        115                 120                 125

Arg Gln Val Leu Asn Ile Thr Gly Ser Ala Pro Ser Val Phe Val Pro
130                 135                 140

Leu Ala Ala Asp Ala Ala Ala Gly Ser Lys Val Ile Thr Val Ala Ala
145                 150                 155                 160

Gly Ala Leu Ser Ala Val Lys Gly Thr Tyr Leu Tyr Leu Arg Ser Asn
                165                 170                 175

Lys Leu Cys Asp Gly Gly Pro Asn Thr Tyr Gly Val Lys Ile Ser Gln
            180                 185                 190

Ile Arg Lys Val Val Gly Val Ser Thr Ser Gly Gly Val Thr Ser Ile
        195                 200                 205

Arg Leu Asp Lys Ala Leu His Tyr Asn Tyr Tyr Leu Ser Asp Ala Ala
210                 215                 220

Glu Val Gly Ile Pro Thr Met Val Glu Asn Val Thr Leu Val Ser Pro
225                 230                 235                 240

Tyr Ile Asn Glu Phe Gly Tyr Asp Asp Leu Asn Arg Phe Phe Thr Ser
                245                 250                 255

Gly Ile Ser Ala Asn Phe Ala Ala Asp Leu His Ile Gln Asp Gly Val
            260                 265                 270

Ile Ile Gly Asn Lys Arg Pro Gly Ala Ser Asp Ile Glu Gly Arg Ser
        275                 280                 285

Ala Ile Lys Phe Asn Asn Cys Val Asp Ser Thr Val Lys Gly Thr Cys
290                 295                 300

Phe Tyr Asn Ile Gly Trp Tyr Gly Val Glu Val Leu Gly Cys Ser Glu
305                 310                 315                 320

Asp Thr Glu Val His Asp Ile His Ala Met Asp Val Arg His Ala Ile
                325                 330                 335

Ser Leu Asn Trp Gln Ser Thr Ala Asp Gly Asp Lys Trp Gly Glu Pro
```

```
                   340                 345                 350
Ile Glu Phe Leu Gly Val Asn Cys Glu Ala Tyr Ser Thr Thr Gln Ala
            355                 360                 365

Gly Phe Asp Thr His Asp Ile Gly Lys Arg Val Lys Phe Val Arg Cys
    370                 375                 380

Val Ser Tyr Asp Ser Ala Asp Asp Gly Phe Gln Ala Arg Thr Asn Gly
385                 390                 395                 400

Val Glu Tyr Leu Asn Cys Arg Ala Tyr Arg Ala Ala Met Asp Gly Phe
            405                 410                 415

Ala Ser Asn Thr Gly Val Ala Phe Pro Ile Tyr Arg Glu Cys Leu Ala
        420                 425                 430

Tyr Asp Asn Val Arg Ser Gly Phe Asn Cys Ser Tyr Gly Gly Gly Tyr
            435                 440                 445

Val Tyr Asp Cys Glu Ala His Gly Ser Gln Asn Gly Val Arg Ile Asn
        450                 455                 460

Gly Gly Arg Val Lys Gly Gly Arg Tyr Thr Arg Asn Ser Ser Ser His
465                 470                 475                 480

Ile Phe Val Thr Lys Asp Val Ala Glu Thr Ala Gln Thr Ser Leu Glu
                485                 490                 495

Ile Asp Gly Val Ser Met Arg Tyr Asp Gly Thr Gly Arg Ala Val Tyr
            500                 505                 510

Phe His Gly Thr Val Gly Ile Asp Pro Thr Leu Val Ser Met Ser Asn
        515                 520                 525

Asn Asp Met Thr Gly His Gly Leu Phe Trp Ala Leu Leu Ser Gly Tyr
    530                 535                 540

Thr Val Gln Pro Thr Pro Arg Met Ser Arg Asn Leu Leu Asp Asp
545                 550                 555                 560

Thr Gly Ile Arg Gly Val Ala Thr Leu Val Ala Gly Glu Ala Thr Val
                565                 570                 575

Asn Ala Arg Val Arg Gly Asn Phe Gly Ser Val Ala Asn Ser Phe Lys
            580                 585                 590

Trp Val Ser Glu Val Lys Leu Thr Arg Leu Thr Phe Pro Ser Ser Ala
        595                 600                 605

Gly Ala Leu Thr Val Thr Ser Val Ala Gln Asn Gln Asp Val Pro Thr
    610                 615                 620

Pro Asn Pro Asp Leu Asn Ser Phe Val Ile Arg Ser Ser Asn Ala Ala
625                 630                 635                 640

Asp Val Ser Gln Val Ala Trp Glu Val Tyr Leu
                645                 650

<210> SEQ ID NO 2
<211> LENGTH: 668
<212> TYPE: PRT
<213> ORGANISM: phage 1611E-K2-1

<400> SEQUENCE: 2

Met Thr Ile Ile Lys Arg Ala Asp Leu Gly Arg Pro Leu Thr Trp Asp
1               5                   10                  15

Glu Leu Asp Asp Asn Phe Gln Gln Val Asp Asp Leu Thr Ala Ala Ala
            20                  25                  30

Ser Ala Ala Val Leu Ser Ala Ser Ala Thr Ala Ala Ala Gly
        35                  40                  45

Ser Ala Thr Asn Ser Leu Asn Ser Ala Asn Ser Ala Ser Ser Ala
    50                  55                  60
```

-continued

Asp Asp Ala Ala Ala Ser Ala Thr Val Ala Ile Asn Ala Leu Met Asn
65                  70                  75                  80

Ser Thr Phe Glu Pro Ala Asp Phe Asp Phe Thr Ser Gly Gly Thr Leu
            85                  90                  95

Asp Ser Thr Asp Arg Asn Lys Ala Val Tyr Asn Pro Ala Asp Asn Asn
        100                 105                 110

Trp Tyr Ser Trp Ser Gly Ile Leu Pro Lys Ile Val Thr Ala Ala Thr
    115                 120                 125

Asp Pro Thr Ala Asp Ser Asn Trp Lys Pro Arg Thr Asp Gln Leu Leu
130                 135                 140

Arg Gln Asn Leu Ala Ser Ser Val Ile Pro Gly Thr Ser Leu Val Thr
145                 150                 155                 160

His Ser Asp Gly Ile His Leu Asp Asp Tyr Ile Glu Ile Phe Asn Arg
                165                 170                 175

Arg Thr Lys Phe Ile Met Pro Glu Asp Phe Pro Gly Thr Asp Thr Glu
            180                 185                 190

Gln Leu Gln Ser Ala Leu Ser Tyr Ala Lys Ser Asn Arg Val Asn Val
        195                 200                 205

Val Leu Gln Ala Gly Lys Thr Tyr Tyr Val Thr Gly Ser Gln Gly Leu
210                 215                 220

Glu Val Asp Leu Gly Tyr Tyr Ser Phe Glu Ser Pro Asn Gly Ile Ala
225                 230                 235                 240

Tyr Ile Asp Phe Thr Gly Cys Thr Ala Thr Tyr Cys Leu Trp Val His
                245                 250                 255

Ser Ser Arg Pro Tyr Pro Asp Gly Ser Glu Asn His Cys Thr Ser Met
            260                 265                 270

Arg Gly Ile Lys Phe Lys Ser Ser Val Lys Gly Ile Gly Gln Arg Leu
        275                 280                 285

Leu Leu Thr Gly Asn Asn Asn Asp Ser Ser Asn Gly Thr Tyr Asn Gly
290                 295                 300

Asp Cys Lys Ile Glu Asn Cys Met Phe Ser Thr Ala Asp Ile Val Leu
305                 310                 315                 320

Gly Ala Ser Asn Ser Thr Trp Arg Tyr Lys Phe Ile Asn Cys Gly Phe
                325                 330                 335

Met Met Glu Ser Thr Gly Gly Thr Tyr Ala Met His Phe Pro Ala Gly
            340                 345                 350

Ile Ser Asp Ser Gly Glu Ser Val Thr Phe Gln Asn Cys Lys Ile Phe
        355                 360                 365

Asp Met Lys Gly Cys Pro Ile Leu Val Glu Cys Ala Ser Phe Ala Ile
370                 375                 380

Gly Met Pro Gly Thr Ser Val Leu Asn Thr Pro Ile Lys Ile Thr Gly
385                 390                 395                 400

Ser Gly Ala Met Val Ile Met Asp Ser Ala Ala Asn Ile Glu Asn Pro
                405                 410                 415

Gly Ala Ser Ala Trp Tyr Arg Tyr Gly Glu Val Thr Gly Thr Gly Ala
            420                 425                 430

Arg Leu Ile Leu Asn Gly Cys Thr Leu Val Cys Asn Asn Pro Ser Leu
        435                 440                 445

Gln Thr Lys Pro Leu Phe Tyr Val Gly Ala Asn Ala Phe Ile Asp Val
        450                 455                 460

Thr Leu Val Lys Thr Pro Gly Asn Asp Tyr Leu Phe Gln Asn Gly Asp
465                 470                 475                 480

Glu Gly Leu Arg Thr Phe Val Glu Gly Asp Gly Tyr Val Thr Ala Ser

```
                    485                 490                 495
His Cys Ile Gly Asp Ile Leu Ser Gly Val Gly Asn Ile Pro Leu His
                500                 505                 510

Lys Ser Leu Asn Pro Thr Leu Asn Pro Gly Phe Glu Thr Gly Asp Leu
            515                 520                 525

Ser Ser Trp Ser Phe Asn Asn Gln Gly Ser Ala Ser Gln Thr Cys Val
        530                 535                 540

Val Gly Thr Ala Tyr Lys Lys Thr Gly Thr Tyr Gly Ala Arg Met Thr
545                 550                 555                 560

Ser Phe Gly Ser Leu Ser Cys Phe Leu Thr Gln Lys Val Lys Val Thr
                565                 570                 575

Gln His Gly Tyr Tyr Ser Thr Thr Cys Gln Ile Asn Thr Ile Thr Ala
            580                 585                 590

Gly Thr Gly Thr Thr Ala Gly Ser Leu Thr Ile Thr Phe Tyr Asn Arg
        595                 600                 605

Asp Gly Asn Ala Leu Gln Ala Gly Ala Ser Ser Asn Phe Thr Asn Thr
    610                 615                 620

Pro Ser Gly Trp Gln Ser Val Gly Arg Phe Ile Gln Gly Arg Val Pro
625                 630                 635                 640

Gln Ala Ala Glu Tyr Cys Glu Val Ser Phe Arg Cys Arg Glu Gly Ala
                645                 650                 655

Val Ile Asp Val Asp Asn Phe Ile Ile Asn Phe Thr
            660                 665

<210> SEQ ID NO 3
<211> LENGTH: 535
<212> TYPE: PRT
<213> ORGANISM: artificial
<220> FEATURE:
<223> OTHER INFORMATION: synthetic polypeptide; a carrier protein

<400> SEQUENCE: 3

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
```

180                 185                 190
Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
        210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 4
<211> LENGTH: 39
<212> TYPE: DNA
<213> ORGANISM: artificial
<220> FEATURE:
<223> OTHER INFORMATION: synthetic polynucleotide; primer 1611E-ORF16-F

<400> SEQUENCE: 4
caaacatcac ggtgacgcta gcatgaccat tatcaaacg                          39

```
<210> SEQ ID NO 5
<211> LENGTH: 38
<212> TYPE: DNA
<213> ORGANISM: artificial
<220> FEATURE:
<223> OTHER INFORMATION: synthetic polynucleotide; primer 1611E-ORF16-R

<400> SEQUENCE: 5
cttttaacat ttagcactcg agtgtaaaat taataatg                            38

<210> SEQ ID NO 6
<211> LENGTH: 21
<212> TYPE: DNA
<213> ORGANISM: artificial
<220> FEATURE:
<223> OTHER INFORMATION: synthetic polynucleotide; primer Ref-K10-1
      ORF6-F

<400> SEQUENCE: 6
atgaataaga tgtttaccca g                                              21

<210> SEQ ID NO 7
<211> LENGTH: 22
<212> TYPE: DNA
<213> ORGANISM: artificial
<220> FEATURE:
<223> OTHER INFORMATION: synthetic polynucleotide; primer Ref-K10-1
      ORF6-R

<400> SEQUENCE: 7
aattgggcga aggcgttcaa ac                                             22
```